(12) United States Patent
Hiraoka et al.

(10) Patent No.: US 10,255,672 B2
(45) Date of Patent: Apr. 9, 2019

(54) MEDICAL APPARATUS AND X-RAY CT SYSTEM

(71) Applicant: Toshiba Medical Systems Corporation, Otawara-shi (JP)

(72) Inventors: Manabu Hiraoka, Nasushiobara (JP);
Go Mukumoto, Utsunomiya (JP);
Katsuhiko Ishida, Nasushiobara (JP);
Naoki Yamashita, Nasushiobara (JP);
Atsushi Fukano, Otawara (JP);
Tatsuya Watanabe, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/774,454

(22) Filed: Feb. 22, 2013

(65) Prior Publication Data

US 2013/0223713 A1    Aug. 29, 2013

(30) Foreign Application Priority Data

Feb. 24, 2012  (JP) .................................. 2012-038352
Mar. 6, 2012   (JP) .................................. 2012-048773

(51) Int. Cl.
*G06T 7/00*     (2017.01)
*A61B 6/00*     (2006.01)
(Continued)

(52) U.S. Cl.
CPC .............. *G06T 7/0012* (2013.01); *A61B 6/12* (2013.01); *A61B 6/463* (2013.01); *A61B 6/466* (2013.01);
(Continued)

(58) Field of Classification Search
CPC ............ A61B 6/032; A61B 6/12; A61B 6/463; A61B 6/466; A61B 6/467; A61B 6/487;
(Continued)

(56) References Cited

U.S. PATENT DOCUMENTS 5,371,778 A * 12/1994 Yanof .................. G06F 3/04845
                                                          128/922
5,734,384 A *  3/1998 Yanof et al. ................... 345/424
(Continued)

FOREIGN PATENT DOCUMENTS

CN   101336843 A    1/2009
CN   101410066 A    4/2009
(Continued)

OTHER PUBLICATIONS

Machine translation of JPO Office Action dated Jan. 5, 2016 for 2012-038352.*
(Continued)

*Primary Examiner* — Katrina R Fujita
(74) *Attorney, Agent, or Firm* — Oblon, McClelland, Maier & Neustadt, L.L.P.

(57) ABSTRACT

A medical apparatus according to an embodiment comprises a setting part, a creating part, and a display controller. The setting part is used for setting an insertion route of a puncture needle for a subject onto an image based on volume data. The creating part creates a graphic schematically indicating the volume data. The display controller displays the graphic on a display, and displays a route image corresponding to the insertion route.

18 Claims, 37 Drawing Sheets

(51) Int. Cl.
  *A61B 34/10* (2016.01)
  *A61B 6/12* (2006.01)
  *A61B 90/00* (2016.01)
  *A61B 6/03* (2006.01)
(52) U.S. Cl.
  CPC .............. *A61B 6/467* (2013.01); *A61B 90/37* (2016.02); *A61B 6/032* (2013.01); *A61B 6/487* (2013.01); *A61B 6/5217* (2013.01); *A61B 2034/107* (2016.02); *A61B 2090/3762* (2016.02)
(58) Field of Classification Search
  CPC . A61B 6/5217; A61B 90/37; A61B 2034/107; A61B 2090/3762; G06T 7/0012
  See application file for complete search history.

(56) References Cited

U.S. PATENT DOCUMENTS

| | | | |
|---|---|---|---|
| 5,740,222 A * | 4/1998 | Fujita | A61B 6/032 378/4 |
| 5,748,696 A * | 5/1998 | Fujita | A61B 6/032 378/205 |
| 5,848,126 A * | 12/1998 | Fujita | A61B 6/032 378/177 |
| 5,986,662 A * | 11/1999 | Argiro et al. | 345/424 |
| 6,064,904 A * | 5/2000 | Yanof et al. | 600/414 |
| 6,380,958 B1 | 4/2002 | Guendel | G06T 15/20 345/427 |
| 6,505,065 B1 * | 1/2003 | Yanof et al. | 600/427 |
| 6,671,538 B1 * | 12/2003 | Ehnholm | A61B 90/10 382/131 |
| 6,891,963 B1 | 5/2005 | Goto et al. | |
| 7,015,935 B2 * | 3/2006 | Herget | A61B 5/055 345/649 |
| 2005/0033160 A1 * | 2/2005 | Yamagata et al. | 600/425 |
| 2007/0055131 A1 * | 3/2007 | Deinzer | A61B 5/416 600/407 |
| 2008/0298660 A1 * | 12/2008 | Yamagata | A61B 6/032 382/131 |
| 2009/0118640 A1 * | 5/2009 | Miller | A61B 90/36 600/567 |
| 2010/0172541 A1 * | 7/2010 | Homan | A61B 90/36 382/103 |

FOREIGN PATENT DOCUMENTS

| | | |
|---|---|---|
| JP | 2002-112998 | 4/2002 |
| JP | 2005-111288 A | 4/2005 |
| JP | 2005-169070 A | 6/2005 |
| JP | 2007-325787 | 12/2007 |
| JP | 2012-29767 A | 2/2012 |

OTHER PUBLICATIONS

Machine translation of JPO Office Action dated Nov. 15, 2015 for 2012-048773.*
Combined Office Action and Search Report dated Aug. 28, 2014 in Chinese Patent Application No. 201310054128.1 (with English translation of category of cited documents).
Office Action dated Jan. 5, 2016 in Japanese Patent Application No. 2012-038352.
Office Action dated Nov. 10, 2015 in Japanese Patent Application No. 2012-048773.

* cited by examiner

MEDICAL APPARATUS AND X-RAY CT SYSTEM

CROSS-REFERENCE TO RELATED APPLICATIONS

This application is based upon and claims the benefit of priority from Japanese Patent Applications No. 2012-038352, filed Feb. 24, 2012 and No. 2012-048773, filed Mar. 6, 2012; the entire contents of all of which are incorporated herein by reference.

FIELD

Embodiments of the present invention relate to a medical apparatus and an X-ray CT system.

BACKGROUND

An X-ray CT (Computed Tomography) system is an apparatus that scans a subject using X-rays, then processes the acquired data by a computer in order to image the inside of the subject.

Specifically, the X-ray CT system radiates X-rays a plurality of times onto a subject from different directions along a circular orbit around the subject. The X-ray CT system detects the X-rays transmitted through the subject by an X-ray detector and acquires a plurality of detected data. The acquired detected data is transmitted to a console device, after being A/D converted by a data acquisition system. The console device applies preprocessing, etc. to this detected data to create projection data. Then, the console device carries out reconstruction processing based on the projection data and creates cross-sectional image data or volume data based on a plurality of cross-sectional image data. The volume data is a data set representing the three-dimensional distribution of CT values corresponding to the three-dimensional region of the subject.

The X-ray CT system can perform MPR (Multi Planar Reconstruction) display by rendering the above-described volume data in an arbitrary direction. Hereinafter, the cross-sectional image that is MPR-displayed via rendering of the volume data is sometimes referred to as a "MPR image." The MPR images include, for example, axial images indicating cross-sections that are orthogonal to the body axis, sagittal images showing lengthwise sections along the body axis, and coronal images showing transverse sections along the body axis. Further, images of arbitrary cross-sections (oblique images) in the volume data are also included in the MPR images. The created multiple MPR images can be simultaneously displayed on the display part, etc.

There is an imaging method referred to as CT fluoroscopy (CTF: Computed Tomography Fluoroscopy) that uses the X-ray CT system. CT fluoroscopy is an imaging method of obtaining images relevant to region of interest of the subject in real time by continuously projecting X-rays onto the subject. According to CT fluoroscopy, images are created in real time by shortening the acquisition rate of the detected data and shortening time required for reconstruction processing. CT fluoroscopy is used, for example, in the confirmation of the positional relation between the point of a puncture needle during a biopsy and the site from which the specimen is obtained, along with the confirmation of the position of the tube when carrying out a drainage method, etc. The drainage method is a method of discharging body fluid accumulated in the body cavities using tubes, etc.

When performing a biopsy on the subject with reference to MPR images based on the volume data obtained from CT fluoroscopy, for example, scanning and puncturing may be alternately carried out. Specifically, at first, MPR images of the subject are obtained from CT fluoroscopy. Doctors, etc., carry out puncturing with reference to these MPR images. In this case, for example, in order to confirm the relational position between the point of the puncture needle and the site from which the specimen is obtained, further CT fluoroscopy is carried out when puncturing is carried out up to a certain stage. With reference to the MPR images obtained from the further CT fluoroscopy, the doctors, etc. progress further with puncturing. This operation is repeatedly carried out until the biopsy is completed.

In addition, when performing a biopsy according to CT fluoroscopy, sometimes a puncture plan is created. The puncture plan is the information including the preset an insertion route (hereinafter, sometimes referred to as a "planned route") of the puncture needle for the subject. The puncture plan, for example, is set in CT images that have been obtained prior to carrying out CT fluoroscopy via drawing of the planned route due to the input of instructions with a mouse, etc. The doctors, etc., carry out puncturing with reference to CT images with the planned routes indicated, as well as MPR images based on the volume data obtained from each X-ray scanning.

In addition, the X-ray CT system can display images schematically indicating the volume data (hereinafter, sometimes referred to as a "viewing box") on the display part together with the MPR images. The cross-sectional positions of the displayed MPR images (to which cross-sections of the volume data of the displayed MPR images correspond) can be displayed in the viewing box.

DETAILED DESCRIPTION

A medical apparatus according to an embodiment comprises a setting part, a creating part, and a display controller. The setting part is used for setting an insertion route of a puncture needle for a subject onto an image based on volume data. The creating part creates a graphic schematically indicating the volume data. The display controller displays the graphic on a display, and displays a route image corresponding to the insertion route.

First Embodiment

With reference to FIGS. 1 to 6, the configuration of the medical apparatus according to the first embodiment will be described. In the present embodiment, an X-ray CT system 1 will be described as an example of the medical apparatus.

Further, as "image" and "image data" correspond to each other in one-to-one fashion, sometimes these are used interchangeably in the present embodiment. In addition, in the present embodiment, an explanation will be provided with the body axial direction of a subject E defined as the Z direction (slice direction), the lateral direction orthogonal to the body axial direction defined as the X direction (channel direction), and the lengthwise direction as the Y direction.

<Configuration of the Apparatus>

Figure 1:
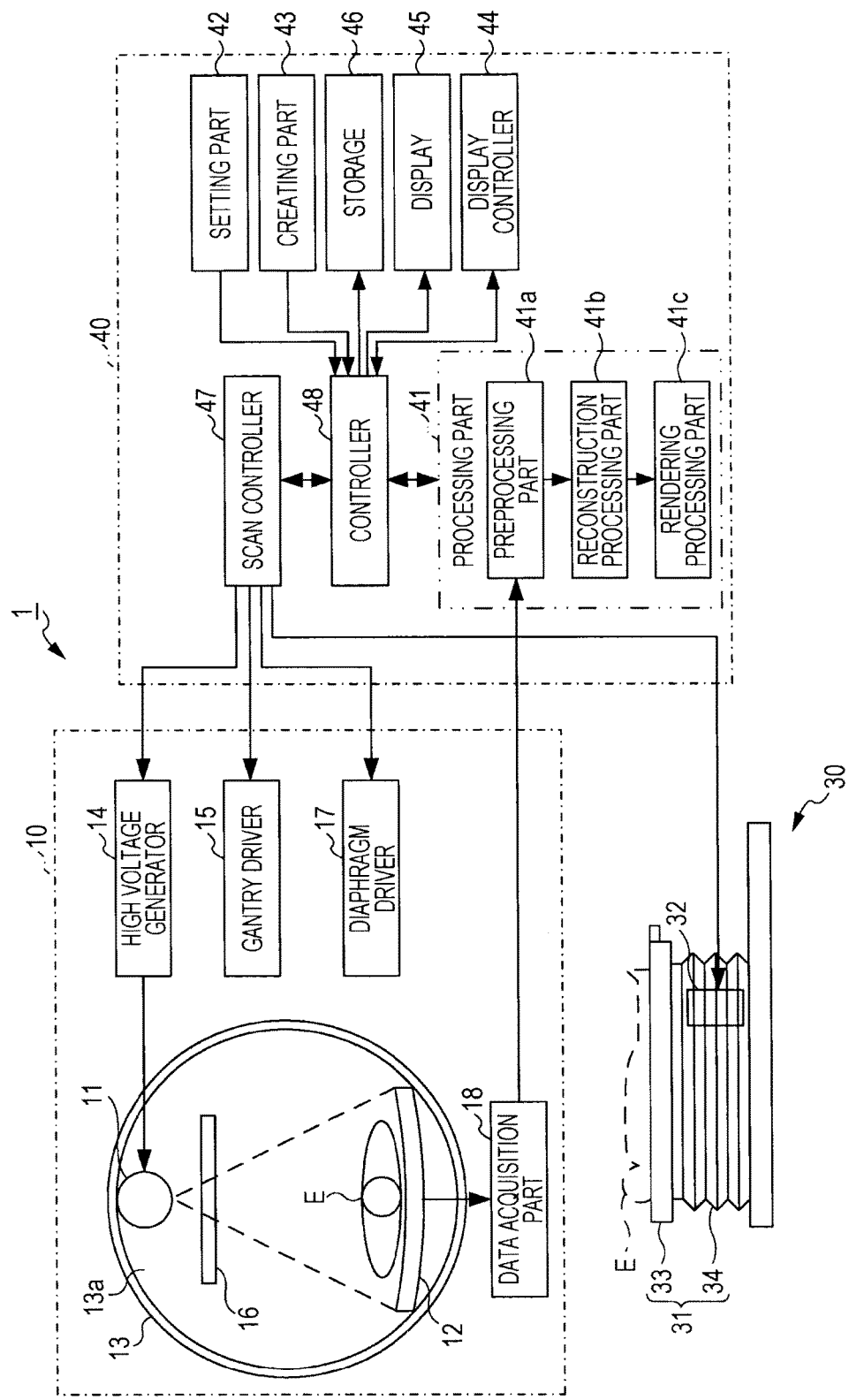
FIG. 1 is a block diagram of the X-ray CT system according to the first embodiment.

As illustrated in FIG. 1, the X-ray CT system 1 comprises a gantry device 10, a bed device 30, and a console device 40.

[Gantry Device]

The gantry device 10 is a device that projects X-rays onto the subject E and acquires the detected data of the X-rays transmitted through the subject E. The gantry device 10 comprises an X-ray generator 11, an X-ray detector 12, a rotational body 13, a high voltage generator 14, a gantry driver 15, an X-ray diaphragm part 16, a diaphragm driver 17, and a data acquisition part 18.

The X-ray generator 11 comprises an X-ray tube that generates X-rays (for example, a vacuum bulb to generate X-ray beams in a conical or pyramid-like shape, not illustrated). The X-ray generator 11 radiates the generated X-rays onto the subject E.

The X-ray detector 12 comprises a plurality of X-ray detection elements (not illustrated). The X-ray detector 12 detects the X-rays transmitted through the subject E. Specifically, the X-ray detector 12 detects X-ray intensity distribution data (hereinafter, sometimes referred to as "detected data") indicating the intensity distribution of X-rays transmitted through the subject E by means of an X-ray detection element, then outputs the detected data as a current signal. As the X-ray detector 12, for example, a two-dimensional X-ray detector (plane detector) is used in which a plurality of detection elements are respectively arranged in two directions (slice direction and channel direction) orthogonal to each other. For example, a plurality of X-ray detection elements are arranged in 320 rows along the slice direction. Thereby, using the X-ray detectors in a plurality of rows, due to a 360-degree scanning roll, a three-dimensional imaging region having a width in the slice direction can be imaged (a volume scan). Further, the slice direction corresponds to the body axial direction of the subject E, while the channel direction corresponds to the rotational direction of the X-ray generator 11.

The rotational body 13 is a member that supports the X-ray generator 11 and the X-ray detector 12 such that they are opposed across the subject E. The rotational body 13 has an opening 13a penetrating therethrough in the slice direction. In the gantry device 10, the rotational body 13 is arranged such that it rotates in a circular orbit around the subject E. In other words, the X-ray generator 11 and the X-ray detector 12 are installed so as to be capable of rotating along a circular orbit around the subject E.

The high voltage generator 14 applies a high voltage to the X-ray generator 11 (hereinafter, "voltage" means the voltage between an anode and a cathode in the X-ray tube). The X-ray generator 11 generates X-rays based on this high voltage.

The gantry driver 15 rotatively drives the rotational body 13. The X-ray diaphragm part 16 has a slit (aperture) of a predetermined width, and adjusts the fan angle (the spread angle in the channel direction) of the X-rays and the cone angle (the spread angle in the slice direction) of the X-rays that are radiated from the X-ray generator 11 by changing the width of the slit. The diaphragm driver 17 drives the X-ray diaphragm part 16 such that the X-rays generated by the X-ray generator 11 are formed into a predetermined shape.

The data acquisition part 18 (DAS: Data Acquisition System) acquires detected data from the X-ray detector 12 (each X-ray detection element). In addition, the data acquisition part 18 converts the acquired detected data (current signals) into voltage signals, amplifies these voltage signals by periodically integrating them, and converts them into digital signals. Then, the data acquisition part 18 transmits the detected data converted into digital signals to the console device 40. Further, in the event of carrying out CT fluoroscopy, the data acquisition part 18 shortens the acquisition rate of the detected data.

[Bed Device]

The bed device 30 is a device for mounting and moving the subject E of an imaging object. The bed device 30 is provided with a bed 31 and a bed driver 32. The bed 31 is provided with a bed top board 33 for mounting the subject E and a base 34 for supporting the bed top board 33. The bed top board 33 can be moved by the bed driver 32 in the body axial direction of the subject E and a direction orthogonal to the body axial direction. In other words, the bed driver 32 can insert and pull the bed top board 33 on which the subject E is mounted into and from an opening 13a of the rotational body 13. The base 34 can move the bed top board 33 vertically (direction orthogonal to the body axial direction of the subject E) using the bed driver 32.

[Console Device]

The console device 40 is used for manipulation and input with respect to the X-ray CT system 1. In addition, the console device 40 has a function, etc. for reconstructing CT image data (cross-sectional image data and volume data) representing the inner morphology of the subject E from the detected data acquired by the gantry device 10. The console device 40 comprises a processing part 41, a setting part 42, a creating part 43, a display controller 44, a display 45, storage 46, a scan controller 47, and a controller 48.

The processing part 41 carries out various processing with respect to the detected data transmitted from the gantry device 10 (data acquisition part 18). The processing part 41 comprises a preprocessing part 41a, a reconstruction processing part 41b, and a rendering processing part 41c.

The preprocessing part 41a creates projection data by carrying out preprocessing such as logarithmic conversion processing, offset correction, sensitivity correction, and beam hardening correction on the detected data detected by the gantry device 10 (X-ray detector 12).

The reconstruction processing part 41b creates CT image data (cross-sectional image data and volume data) based on the projection data created in the preprocessing part 41a. In order to reconstruct the cross-sectional image data, any method, for example, a two-dimensional Fourier transformation method, a convolution/back projection method, etc. can be adopted. The volume data is created by interpolating a plurality of reconstructed cross-sectional image data. In order to reconstruct the volume data, for example, any method such as a cone beam reconstruction method, a multi-slice reconstruction method, an enlarged reconstruction method, etc. can be adopted. As described above, due to volume scanning using the X-ray detectors in multiple rows, it is possible to reconstruct the volume data over a wide range. In addition, in the event of carrying out CT fluoroscopy, as the acquisition rate of the detected data is made shorter, the reconstruction time by the reconstruction processing part 41b is shortened. Accordingly, CT image data corresponding to the scanning can be created in real time.

The rendering processing part 41c carries out the rendering processing for the volume data created in the reconstruction processing part 41b.

For example, the rendering processing part 41c creates a pseudo three-dimensional image (image data) by applying volume rendering processing to the volume data. The "pseudo three-dimensional image" is an image for two-dimensionally displaying the three-dimensional structure of the subject E.

In addition, the rendering processing part 41c creates an MPR image (image data) by applying rendering processing to the volume data in the desired direction. The "MPR image" is an image indicating the desired cross-section of the subject E. The MPR images include three orthogonal cross-sections, that is, an axial image, a sagittal image and a coronal image. Alternatively, the rendering processing part 41c may create an oblique image indicating an arbitrary cross-section as an MPR image.

The setting part 42 is used for setting an insertion route of a puncture needle for the subject E onto the image based on the volume data. The insertion route to be set is a route (a planned route) indicating the route along which the puncture needle is inserted in the subject E.

As a specific example of the setting part 42, the case will be described in which the insertion route I is set for the MPR image based on the volume data (first volume data) obtained from the scan made at a certain timing (first scan). Hereinafter, an explanation will be provided using the axial image as an example of the MPR image; however, the configuration of the present embodiment can be applied to the sagittal image or the coronal image as well as the axial image.

Figure 2A:
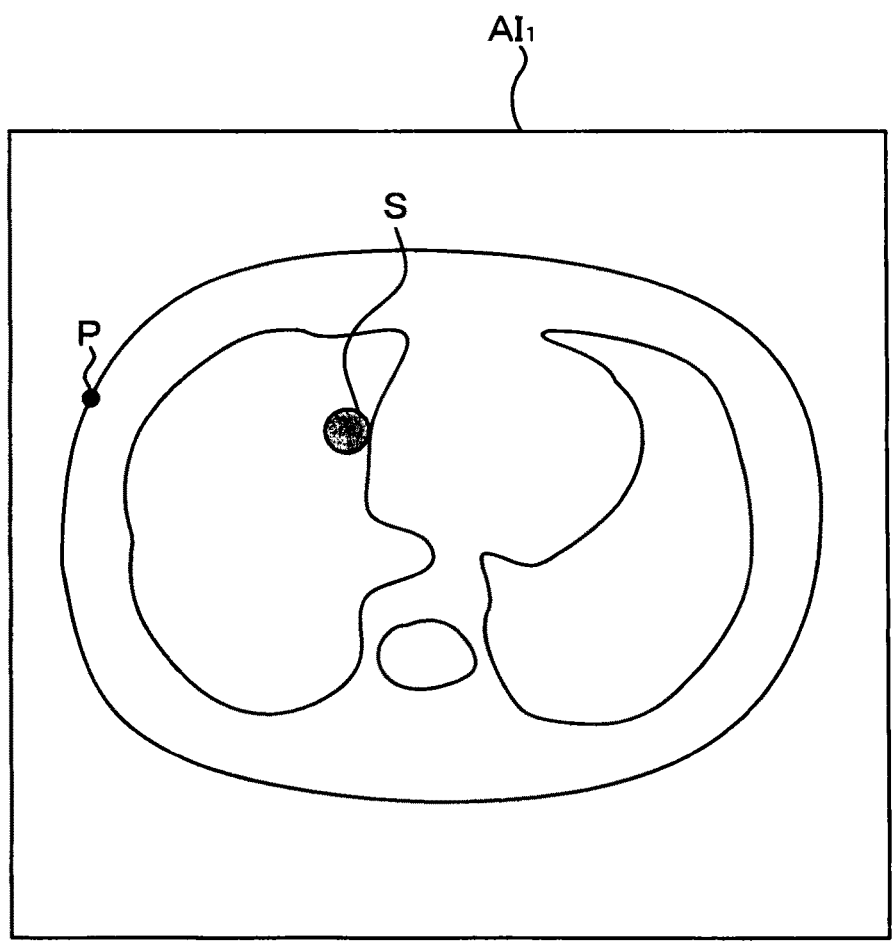
FIG. 2A is a diagram supplementing the explanation of the setting part according to the first embodiment.
Figure 2B:
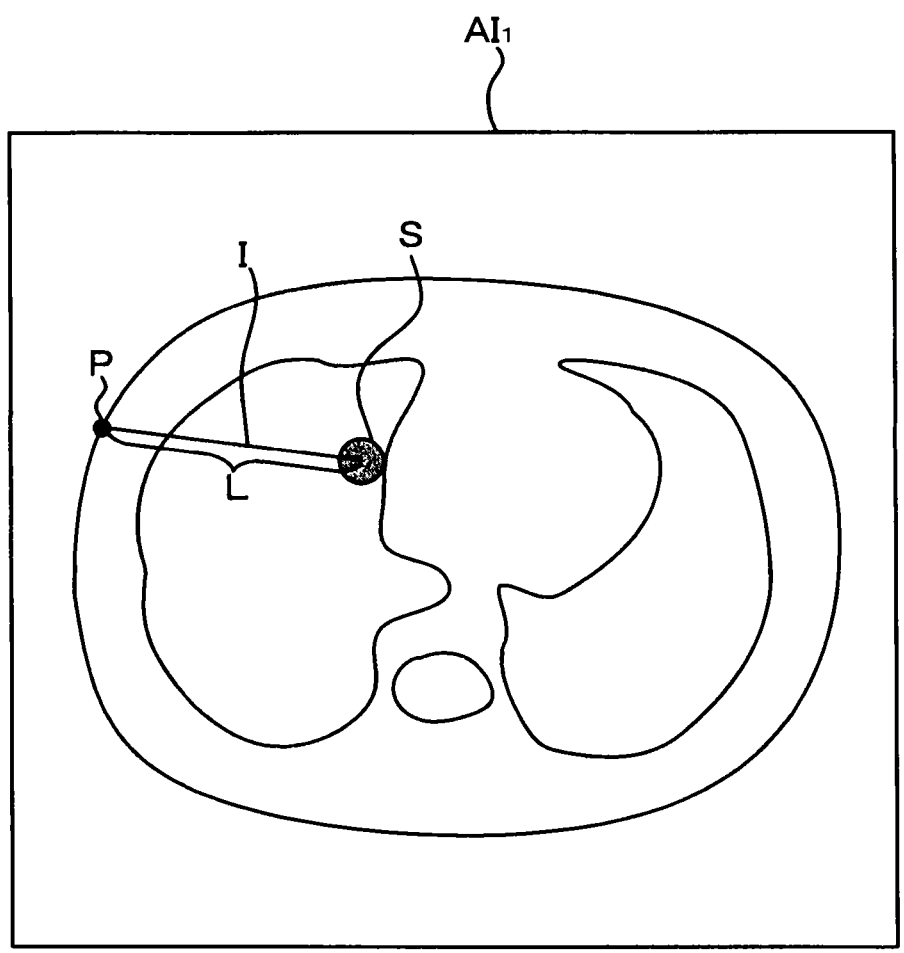
FIG. 2B is a diagram supplementing the explanation of the setting part according to the first embodiment.

FIG. 2A and FIG. 2B illustrate an axial image $AI_1$ which is a cross-section in the Z direction based on the first volume data.

Using an input device (not illustrated), etc., the operator designates two points, namely, the position S of an object site (a lesion, etc.) where a biopsy is carried out and the insertion position P of the puncture needle on the body surface corresponding to the axial image $AI_1$ displayed on the display 45 (refer to FIG. 2A). The setting part 42 calculates the shortest distance L connecting these two points, and sets a line segment connecting this shortest distance L as the insertion route I (refer to FIG. 2B). The set insertion route I (coordinate values) is stored in the storage 46. The axial image $AI_1$ is an image based on three-dimensional volume data. Accordingly, the insertion route I set in the axial image $AI_1$ can be identified by three-dimensional coordinate values.

Further, the operator can also directly draw a line segment, etc. indicating the insertion route on the axial image $AI_1$ using the input device, etc. In this case, the setting part 42 sets this drawn line segment as the insertion route I. Alternatively, the setting part 42 carries out image analysis processing such as a region-growing method on the axial image $AI_1$ to calculate the position of the lesion and the position on the body surface nearest to the lesion. Then, the setting part 42 can also calculate a line segment connecting these positions and subsequently set this line segment as the insertion route I.

In addition, the images onto which the insertion route I is set are not limited to the MPR images. For example, the setting part 42 can also set the insertion route I onto the pseudo three-dimensional images based on the volume data (images for two-dimensionally displaying the three-dimensional structure) by the same method as above.

The creating part 43 creates a graphic schematically indicating the volume data (hereinafter, referred to as a "viewing box"). Further, the viewing box created by the creating part 43 and a pseudo three-dimensional image of the viewing box displayed on the display 45 by the display controller 44 correspond to each other in one-to-one fashion; therefore, sometimes these are identified in the present embodiment. In addition, the form of the volume data is decided based on the size of the X-ray detector 12, the scan range, etc.

As a specific example of the creating part 43, the case of creating a viewing box V based on volume data D will be described. Here, the volume data D is represented as a cube, that is, a rectangular parallelepiped in which all sides have the same length. In addition, it is assumed that the viewing box V and the volume data D are defined by the same coordinate system. At first, the creating part 43 extracts the outline part O of the volume data D according to a method such as edge detection, etc. (refer to FIG. 3A). Next, the creating part 43 creates a viewing box V by converting the extracted outline part O into a predetermined scale size (refer to FIG. 3B). The scale size is, for example, a value to be set in advance based on the display region, etc. of the viewing box V on the display 45.

Figure 3A:
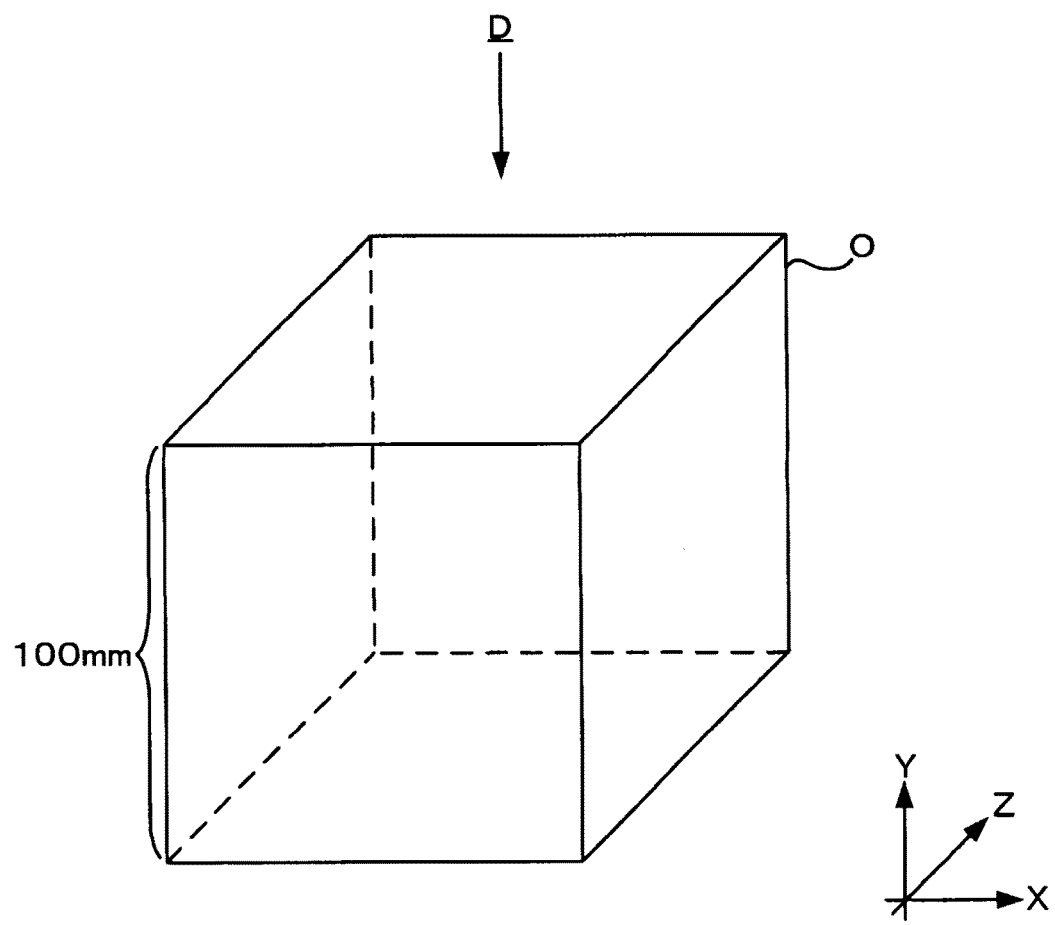
FIG. 3A is a diagram supplementing the explanation of the creating part according to the first embodiment.

In the present embodiment, the creating part 43 creates a viewing box V such that the scale sizes of respective sides of the volume data D are identical. For example, the case in which the scale size is set to be 1/10 will be described. As illustrated in FIG. 3A, if the length of the sides of the volume data D (the outline part O) is 100 mm, the creating part 43 creates a viewing box V formed in a cubic shape with the length of the sides thereof being 10 mm based on the scale size 1/10.

Figure 3B:
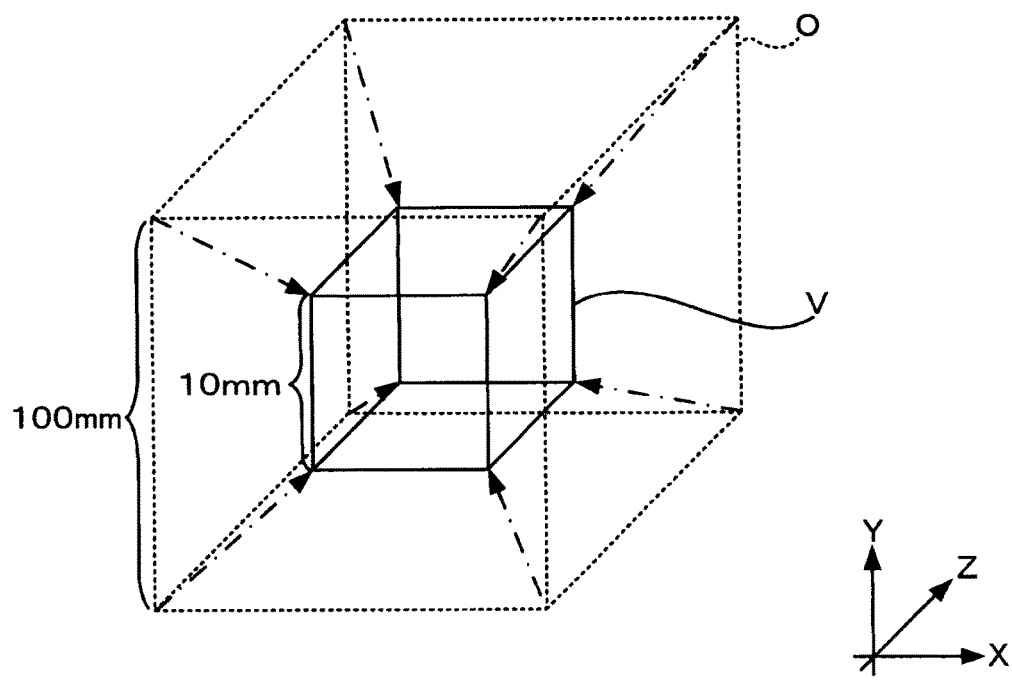
FIG. 3B is a diagram supplementing the explanation of the creating part according to the first embodiment.
Figure 4:
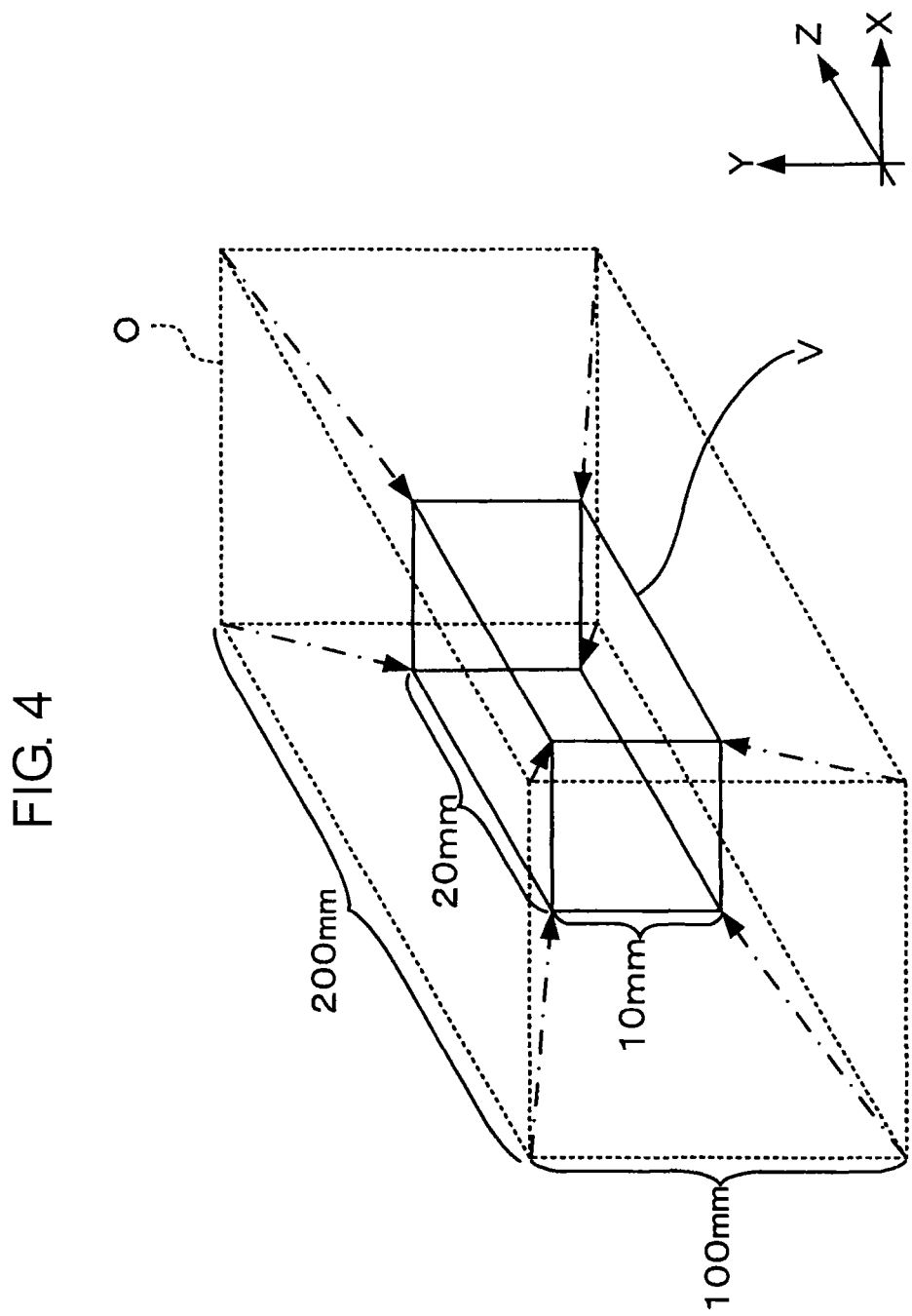
FIG. 4 is a diagram supplementing the explanation of the setting part according to the first embodiment.

Further, in FIG. 3A and FIG. 3B, an example in which, when the shape of the volume data D is a cube, the shape of the viewing box V is also a cube (namely, an example of creating the viewing box such that respective sides thereof are of identical scale size) is illustrated. Here, using the X-ray detection elements in multiple rows, compared to the X direction and the Y direction, it is possible to set a wider detection range in the body axial direction (Z direction). As a result, the shape of the obtained volume data may also become a rectangular parallelepiped in which the length of the sides in the Z direction, and the length of the sides in the X direction and the length of the sides in the Y direction are different from each other. In this case, the creating part 43 creates a viewing box V with a shape of a rectangular parallelepiped based on the shape of the volume data (rectangular parallelepiped). For example, as illustrated in FIG. 4, it is assumed that volume data D (the outline part O) is obtained in which the length of the sides in the X direction and the Y direction is 100 mm, and the length of the sides in the Z direction is 200 mm. In this case, based on the scale size (for example, 1/10) set in advance, the creating part 43 creates a viewing box V in which the length of the sides in the X direction and the Y direction is 10 mm, and the length of the sides in the Z direction is 20 mm (refer to FIG. 4).

The display controller 44 carries out various controls regarding the image display. For example, it carries out the control to display pseudo three-dimensional images and MPR images, etc. created by the rendering processing part 41c on the display 45.

In addition, in the present embodiment, the display controller 44 displays a graphic (the viewing box V) on the display 45, and displays the route image I' corresponding to the insertion route I on the graphic (the viewing box V).

Figure 3C:
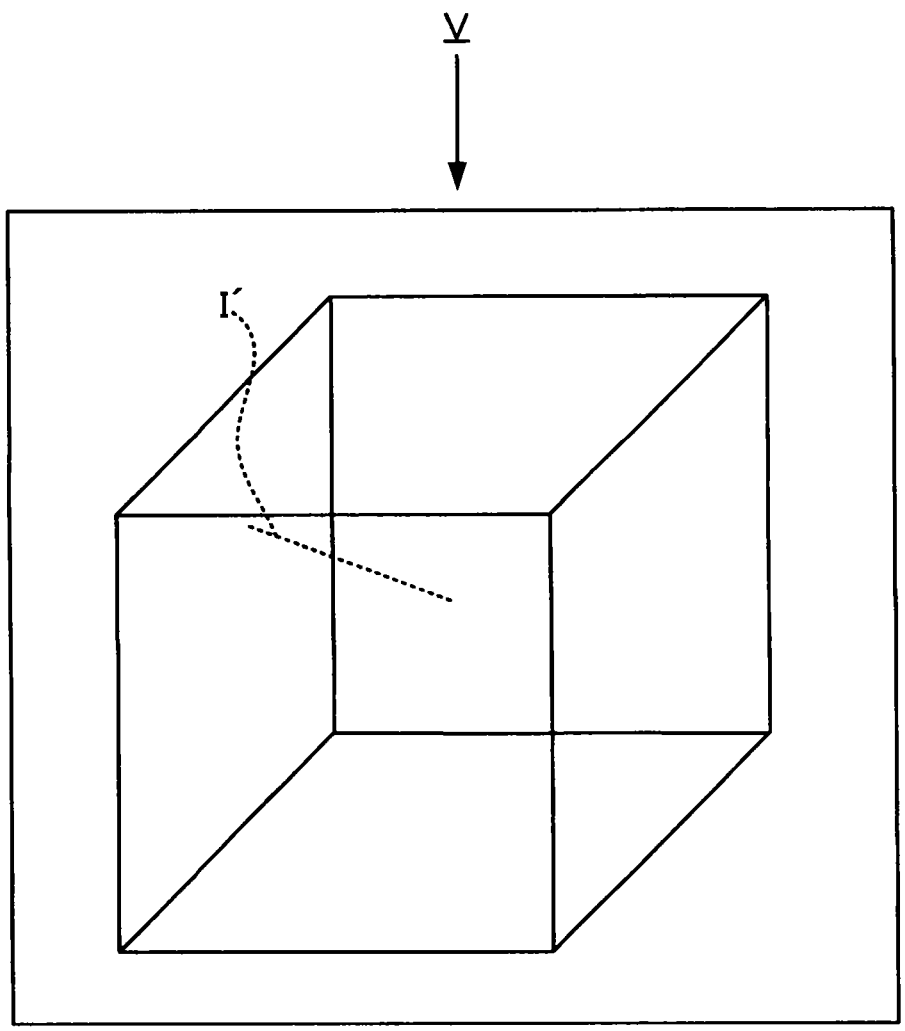
FIG. 3C is a diagram supplementing the explanation of the display controller according to the first embodiment.

Specifically, the display controller 44 displays the created viewing box V on the display 45 as a pseudo three-dimensional image. Further, the display controller 44 creates route image I' by converting the insertion route I stored in the storage 46 into the same scale size as that when creating the viewing box V. The display controller 44 displays the created route image I' in the viewing box V (refer to FIG. 3C; FIG. 3C illustrates the viewing box V displayed on the display 45). The route image I' is an example of "information regarding a puncture plan."

As described above, the viewing box V and the volume data D (the outline part O) are defined by the same coordinate system. Accordingly, the position and direction of the route image I' to be displayed in the viewing box V, and the position and direction of the insertion route I in the volume data D are correspondingly related. In other words, the operator can easily grasp information (position and direction) about the planned route (the insertion route I) by referring to the viewing box V displayed on the display 45.

The display 45 comprises an arbitrary display device such as an LCD (Liquid Crystal Display) and a CRT (Cathode Ray Tube) display, etc. For example, the MPR images obtained by rendering volume data are displayed on the display 45.

Figure 5:
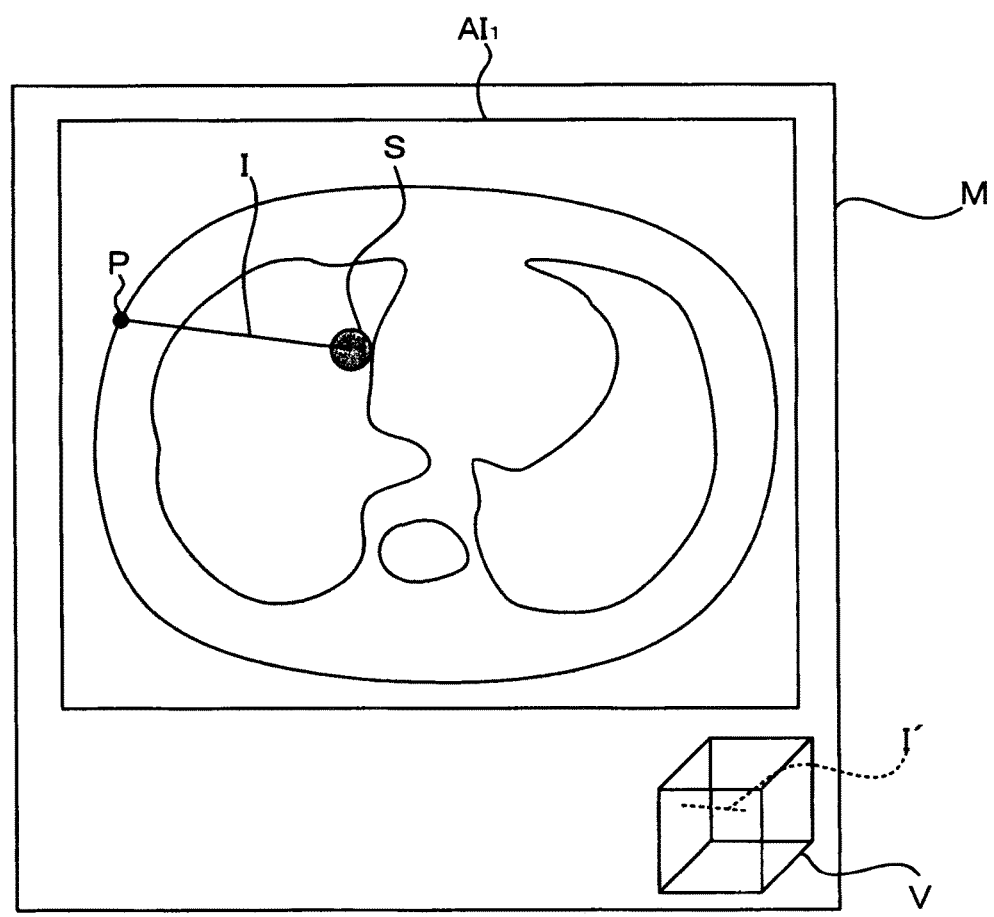
FIG. 5 is a diagram supplementing the explanation of the display according to the first embodiment.

FIG. 5 is an example of a display screen M on the display 45. Here, an example in which the axial image $AI_1$ with the insertion route I planned is displayed on the display screen M will be described. The display controller 44 displays the viewing box V (route image I') at a predetermined display position on the display screen M. The display position of the viewing box V may be set in advance or can be optionally set using the input device, etc. Further, when a plurality of MPR images are displayed on the display 45, the display controller 44 can display the viewing box V for each MPR image. For example, when the axial image, the sagittal image and the coronal image are displayed, the display controller 44 displays the viewing box V for each of the images.

The storage 46 comprises a semiconductor storing device such as RAM, ROM, etc. The storage 46 stores the detected data, the projection data, and the CT image data after reconstruction processing, other than the setting position of the insertion route.

The scan controller 47 controls various operations regarding X-ray scanning. For example, the scan controller 47 controls the high voltage generator 14 to apply a high voltage to the X-ray generator 11. The scan controller 47 controls the gantry driver 15 to rotatively drive the rotational body 13. The scan controller 47 controls the diaphragm driver 17 to operate the X-ray diaphragm part 16. The scan controller 47 controls the bed driver 32 to move the bed 31.

The controller 48 carries out overall control of the X-ray CT system 1 by controlling operations of the gantry device 10, the bed device 30 and the console device 40. For example, the controller 48 causes the gantry device 10 to carry out preliminary scanning as well as main scanning and to acquire the detected data by controlling the scan controller 47. In addition, the controller 48 controls the processing part 41 to carry out various processing (preprocessing, reconstruction processing, etc.) on the detected data. In addition, the controller 48 controls the display controller 44 to display, on the display 45, the images based on the CT image data, etc. stored in the storage 46.

<Operation>

Figure 6:
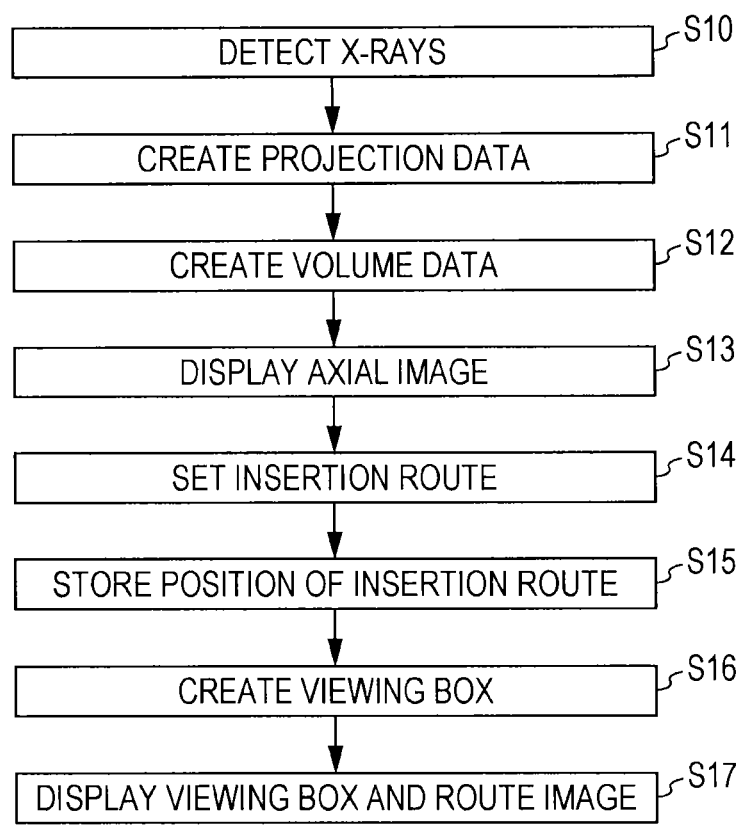
FIG. 6 is a flowchart showing the summary of the operation of the X-ray CT system according to the first embodiment.

Next, with reference to FIG. 6, the operation of the X-ray CT system 1 according to the present embodiment will be described.

At first, the X-ray CT system 1 carries out X-ray scanning on the subject E to create first volume data.

Specifically, the X-ray generator 11 radiates X-rays onto the subject E. The X-ray detector 12 detects the X-rays transmitted through the subject E, and acquires the detected data (S10). The detected data obtained by the X-ray detector 12 is acquired by the data acquisition part 18 and is transmitted to the processing part 41 (the preprocessing part 41*a*).

The preprocessing part 41*a* carries out preprocessing such as logarithmic conversion processing, offset correction, sensitivity correction, and beam hardening correction to the detected data obtained in S10, and creates projection data (S11). The created projection data is transmitted to the reconstruction processing part 41*b* based on the control of the controller 48.

The reconstruction processing part 41*b* creates a plurality of cross-sectional image data based on the projection data created in S11. In addition, the reconstruction processing part 41*b* creates first volume data by interpolating the plurality of cross-sectional image data (S12).

The rendering processing part 41*c* creates an axial image $AI_1$ by rendering the first volume data created in S12. The display controller 44 displays the created axial image $AI_1$ on the display 45 (S13).

The operator makes a plan (a planned route) for the insertion route I of the puncture needle by referring to the axial image $AI_1$ displayed on the display 45. The operator designates the position of a lesion in the axial image $AI_1$, and the insertion position of the puncture needle using the input device, etc. The setting part 42 sets a line segment connecting the designated positions as the insertion route I (S14). The setting part 42 transmits the coordinate values of the insertion route I to the storage 46. The storage 46 stores the insertion route I (coordinate values) (S15).

In addition, the creating part 43 creates a viewing box V by converting the first volume data created in S12 into a predetermined scale size (S16).

The display controller 44 displays the viewing box V created in S16 on the display 45, and displays the route image I' corresponding to the insertion route I stored in S15 at the corresponding position of the viewing box V (S17).

Further, the processing part 41, the setting part 42, the creating part 43, the display controller 44, the scan controller 47, and the controller 48 may be configured by, for example, a processing device (not illustrated) such as a CPU (Central Processing Unit), a GPU (Graphic Processing Unit), and an ASIC (Application Specific Integrated Circuit), and a storing device (not illustrated) such as ROM (Read Only Memory), RAM (Random Access Memory), and HDD (Hard Disc Drive). A processing program for carrying out the function of the processing part 41 is stored in the storing device. In addition, a setting processing program for carrying out the function of the setting part 42 is stored in the storing device. In addition, a creation program for carrying out the function of the creating part 43 is stored in the storing device. In addition, a display control program for carrying out a function of the display controller 44 is stored in the storing device. Further, a scan control program for carrying out the function of the scan controller 47 is stored in the storing device. In addition, a control program for carrying out the function of the controller 48 is stored in the storing device. A processing device such as a CPU carries out the functions of respective parts by carrying out respective programs stored in the storing device.

<Operation and Effect>

The operation and the effect of the present embodiment will be described.

The X-ray CT system 1 of the present embodiment creates volume data based on the results obtained from scanning the subject E using X-rays. The X-ray CT system 1 has the setting part 42, the creating part 43, and the display controller 44. The setting part 42 is used for setting the insertion route I of the puncture needle for the subject E to the image based on the volume data. The creating part 43 creates a graphic (viewing box V) schematically indicating the volume data. The display controller 44 displays the graphic on the display 45, and displays the route image I' corresponding to the insertion route I on the graphic.

Specifically, the creating part 43 creates the graphic such that the scale sizes of the respective sides are identical based on the shape of the volume data.

Thus, the display controller 44 displays the viewing box V on the display 45, and displays the route image I' corresponding to the insertion route I on the viewing box V. The viewing box V is an image obtained by converting the respective sides of the volume data D into the same scale size. Therefore, the route image I' is displayed in the position (direction) of the viewing box V corresponding to the position (direction) of the insertion route I in the volume data D. The operator can grasp the position (direction) of the planned route (insertion route I) by confirming the viewing box V on which the route images I' is displayed. In other words, the X-ray CT system 1 in the present embodiment can present information regarding the puncture plan.

Second Embodiment

Next, with reference to FIGS. 7A to 9, the configuration of the X-ray CT system 1 (an example of the medical apparatus) according to the second embodiment will be described. In the present embodiment, the configuration of displaying, on the viewing box V, the cross-sectional position corresponding to the MPR image on which the insertion route I is set will be described. The cross-sectional position corresponding to the MPR image on which the insertion route I is set is an example of "information regarding a puncture plan." With respect to configuration identical with the first embodiment, a detailed explanation thereof is omitted.

In the present embodiment, the setting part 42 derives the position (coordinate values) of the MPR image with the insertion route I set in the volume data. This position is stored in the storage 46.

In the present embodiment, the display controller 44 displays the graphic (viewing box) on the display 45, and displays the cross-sectional position corresponding to the MPR image with the insertion route I set on the graphic (viewing box).

Specifically, the display controller 44 displays the viewing box V created by the creating part 43 on the display 45 as a pseudo three-dimensional image. Further, the display controller 44 converts the position (coordinate values) of the MPR image stored in the storage 46 into the same scale size as that when creating the viewing box V. Then, the display controller 44 identifies the position in the viewing box V corresponding to the converted value as a cross-sectional position. The display controller 44 displays the cross-sectional position in the viewing box V.

Figure 7A:
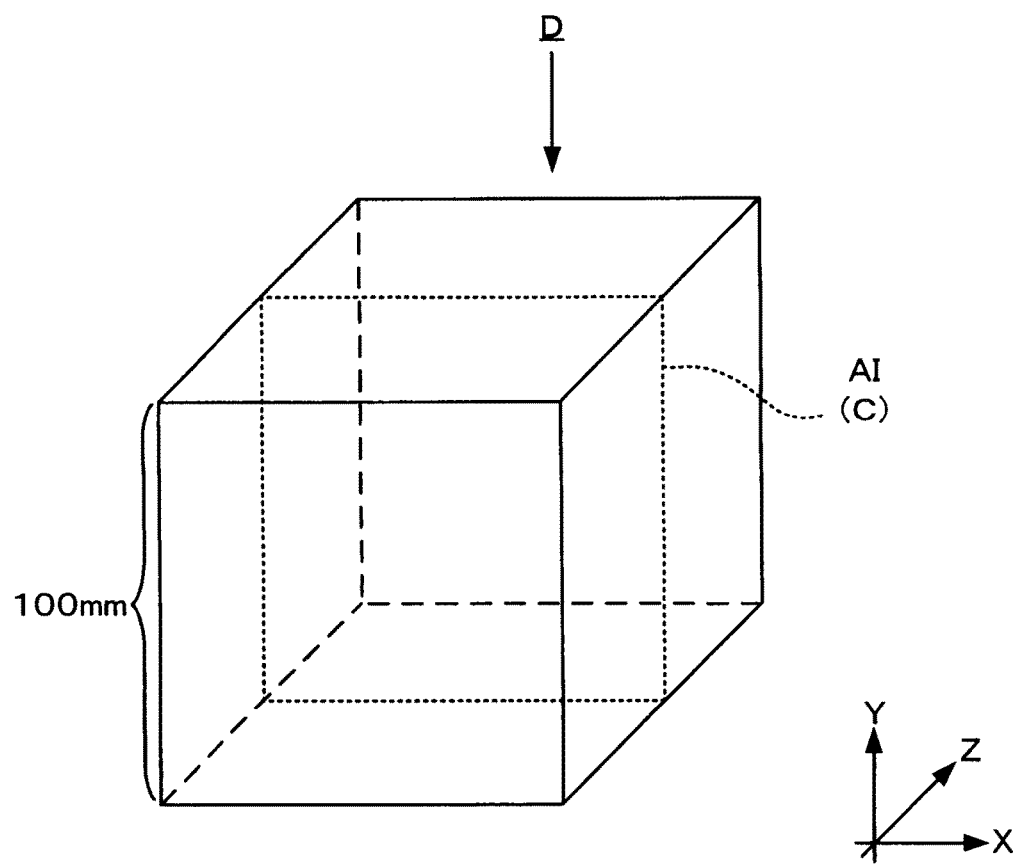
FIG. 7A is a diagram supplementing the explanation of the display controller according to the second embodiment.
Figure 7B:
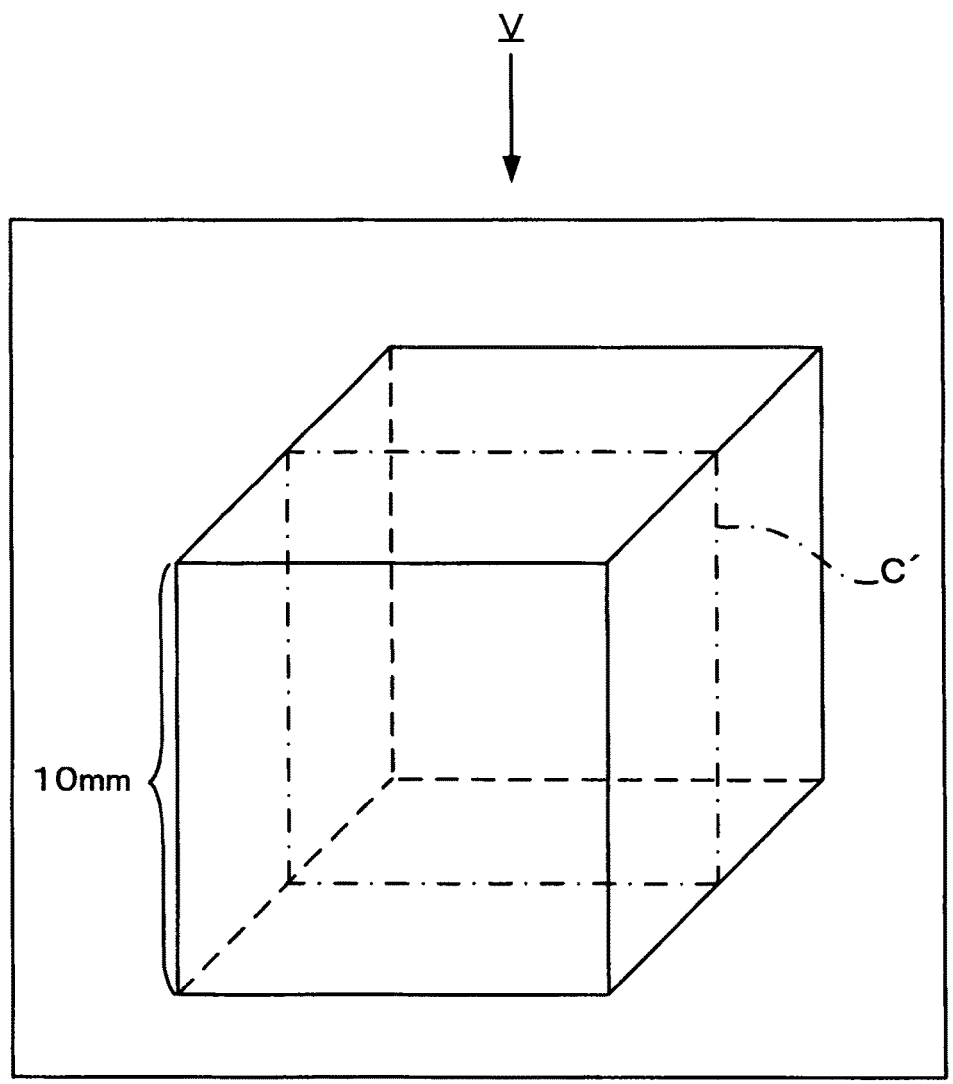
FIG. 7B is a diagram supplementing the explanation of the display controller according to the second embodiment.

For example, it is assumed that the insertion route I is set based on the axial image AI at a position C of the volume data D (refer to FIG. 7A). In this case, if the scale size of the viewing box V is $\frac{1}{10}$, the display controller 44 converts the position C into the scale size $\frac{1}{10}$, and identifies the position in the corresponding viewing box V as cross-sectional position C'. Then, the display controller 44 displays the cross-sectional position C' in the viewing box V (refer to FIG. 7B, FIG. 7B illustrates the viewing box V displayed on the display 45). The viewing box V and the volume data D are defined by the same coordinate system. Accordingly, the position of the cross-sectional position C' displayed in the viewing box V and the position C of the axial image AI in the volume data D are correspondingly related. In other words, the operator can easily grasp the position of the MPR image with the insertion route I set by referring to the viewing box V displayed on the display 45.

<Operation>

Figure 8:
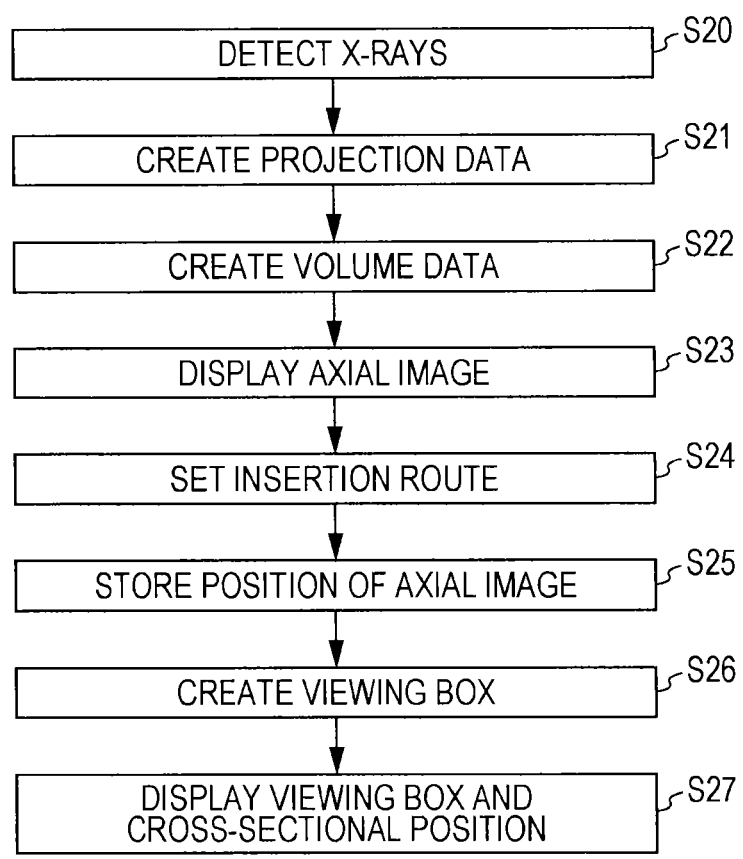
FIG. 8 is a flowchart showing the summary of the operation of the X-ray CT system according to the second embodiment.

Next, with reference to FIG. 8, the operation of the X-ray CT system 1 according to the present embodiment will be described.

At first, the X-ray CT system 1 carries out X-ray scanning on the subject E to create first volume data.

Specifically, the X-ray generator 11 radiates X-rays onto the subject E, the X-ray detector 12 detects the X-rays transmitted through the subject E, and acquires the detected data (S20). The preprocessing part 41$a$ carries out preprocessing such as logarithmic conversion processing, offset correction, sensitivity correction, and beam hardening correction on the detected data acquired in S20, and creates projection data (S21). The reconstruction processing part 41$b$ creates a plurality of cross-sectional image data based on the projection data created in S21. In addition, the reconstruction processing part 41$b$ creates first volume data by interpolating the plurality of cross-sectional image data (S22). The rendering processing part 41$c$ creates axial images AI$_1$ by rendering the first volume data created in S22. The display controller 44 displays the created axial images AI$_1$ on the display 45 (S23).

The operator makes a plan (planned routes) for the insertion route I of the puncture needle by referring to the axial images AI$_1$ displayed on the display 45. The operator designates the position of a lesion in the axial image AI$_1$, and the insertion position of the puncture needle using the input device, etc. The setting part 42 sets a line segment connecting the designated positions as the insertion route I (S24). The setting part 42 transmits the position C of the axial image AI$_1$ with the insertion route I set to the storage 46. The storage 46 stores the position C of the axial image AI$_1$ with the insertion route I set (S25).

In addition, the creating part 43 creates a viewing box V by converting the first volume data created in S22 into the predetermined scale size (S26).

The display controller 44 displays the viewing box V created in S26 on the display 45, and displays the cross-sectional position C' corresponding to the position C stored in S25 at the corresponding position of the viewing box V (S27).

Further, the display controller 44 can display the route image I' in the viewing box V together with the cross-sectional position C'.

In this case, the setting part 42 derives the position (coordinate values) of the MPR image with the insertion route I set in the volume data, and derives the insertion route I (coordinate values) in this MPR image. These coordinate values are stored in the storage 46.

Figure 9:
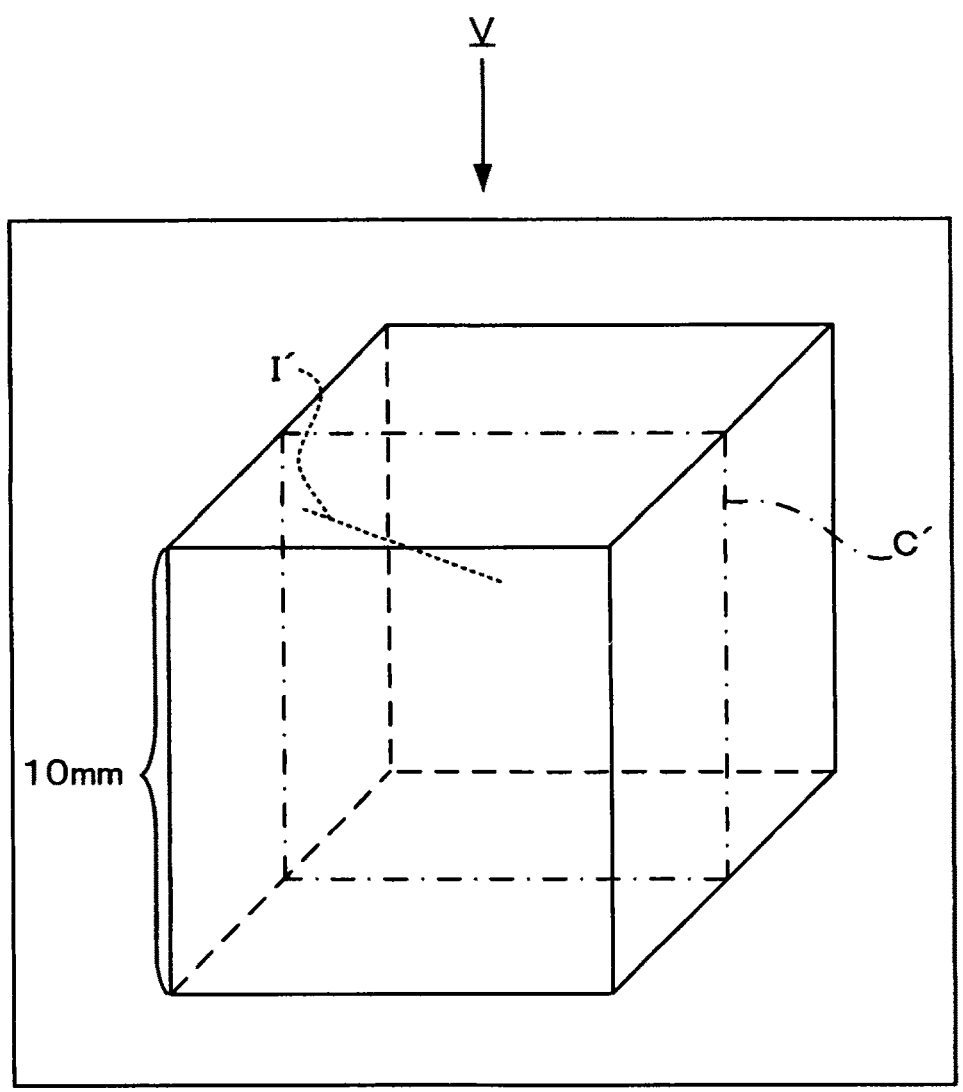
FIG. 9 is a diagram supplementing the explanation of the display controller according to the second embodiment.

The display controller 44 displays the viewing box V created by the creating part 43 on the display 45 as pseudo three-dimensional images. In addition, the display controller 44 creates a route image I' by converting the insertion route I stored in the storage 46 into the same scale size as that when creating the viewing box V. Further, with respect to the positions of the MPR images stored in the storage 46, the display controller 44 identifies the position converted into the same scale size as that when creating the viewing box V as the cross-sectional position C'. The display controller 44 displays the route image I' and the cross-sectional position C' in the viewing box V (refer to FIG. 9; FIG. 9 illustrates the viewing box V displayed on the display 45).

<Operation and Effect>

The operation and the effect of the present embodiment will be described.

The X-ray CT system 1 of the present embodiment creates volume data based on the results obtained from scanning the subject E using X-rays. The X-ray CT system 1 has the setting part 42, the creating part 43, and the display controller 44. The setting part 42 is used for setting an insertion route I of the puncture needle for the subject E to the MPR image based on the volume data. The creating part 43 creates a graphic (viewing box) schematically indicating the volume data. The display controller 44 displays the graphic on the display 45, and displays the cross-sectional position C' corresponding to the MPR image with the insertion route I set on the graphic.

In addition, the X-ray CT system 1 of the present embodiment creates volume data based on the results obtained from scanning the subject E using X-rays. The X-ray CT system 1 has the setting part 42, the creating part 43, and the display controller 44. The setting part 42 is used for setting an insertion route I of the puncture needle for the subject E to the MPR image based on the volume data. The creating part 43 creates a graphic (viewing box) schematically indicating the volume data. The display controller 44 displays the graphic on the display 45, and displays the route image I' corresponding to the insertion route I and the cross-sectional position C' corresponding to the MPR image with the insertion route I set on the graphic.

Thus, the display controller 44 displays the viewing box V on the display 45, and displays the cross-sectional position C' corresponding to the MPR image with the insertion route I set (and the route image I') on the viewing box V. Accordingly, the operator can grasp the position of the image used for setting the insertion route I (and the position of the planned route) by confirming the viewing box V on which the cross-sectional position C' (and the route image I') are displayed. In other words, the X-ray CT system 1 in the present embodiment can present information regarding the puncture plan.

Third Embodiment

With reference to FIGS. 10A to 12, the configuration of the X-ray CT system 1 (an example of the medical apparatus) according to the third embodiment will be described. In the present embodiment, the configuration of displaying the cross-sectional position corresponding to the position of the currently displayed MPR image on the viewing box V will be described. With respect to the configuration identical with the above-described embodiments, a detailed explanation thereof is omitted. In addition, the present embodiment will be described based on the configuration of the second embodiment; however, the present embodiment can be applied to the configuration of the first embodiment.

In the present embodiment, the display controller 44 displays the cross-sectional positions corresponding to an MPR image based on other volume data (second volume data) different from the first volume data on the viewing box V. Other volume data, for example, is data created based on scanning (second scan) at a different timing from that of the first scan.

As a specific example, the case of displaying the cross-sectional position c' corresponding to the axial image $AI_2$ based on the second volume data on the viewing box V will be described. Here, the status wherein the axial image $AI_1$ with the insertion route I set and the viewing box V with the cross-sectional position C displayed are displayed at predetermined display positions on the display screen M will be described (refer to FIG. 10A). The cross-sectional position C' is, as well as the second embodiment, the position corresponding to the position C of the axial image $AI_1$ with the insertion route I set.

According to the present embodiment, in the first volume data and the second volume data, it is assumed that the number of pieces of cross-sectional image data from which respective volume data originate is identical and the number of pixels of the images is also identical. In addition, it is assumed that the imaging conditions (the imaging position, the rotation speed of the rotational body 13, etc.) of the first scan and the second scan are also identical. In other words, it is assumed that the first volume data and the second volume data are defined by the same coordinate system.

In the event that the second scan is carried out, the rendering processing part 41c creates axial images $AI_2$ at the position c set in advance (or the position designated by the input device, etc.) to the second volume data based on the obtained detected data. The created axial image $AI_2$ is displayed on the display 45 (display screen M) by the display controller 44 (refer to FIG. 10B).

In addition, the display controller 44 identifies the cross-sectional position c' corresponding to the position c of the axial image $AI_2$ in the viewing box V. As described above, the first volume data and the second volume data are defined by the same coordinate system. Accordingly, the second volume data and the viewing box V are also defined by the same coordinate system. In other words, the display controller 44 can identify the cross-sectional position c' by converting the position c into the scale size when creating the viewing box V. Then, the display controller 44 displays the cross-sectional position c' corresponding to the position c of the axial image $AI_2$ on the viewing box V (refer to FIG. 10B).

Here, when the cross-sectional position C' is identical with the cross-sectional position c', the axial image $AI_1$ that is used for planning the insertion route I and the currently displayed axial image $AI_2$ are also identical with each other. Accordingly, when puncturing is carried out along the planned insertion route I, the puncture needle is displayed on the currently displayed axial image $AI_2$. Accordingly, the operator can grasp whether or not puncturing has been promoted according to the plan.

On the contrary, when the cross-sectional position C' and the cross-sectional position c' deviate from each other (the case of FIG. 10B), the axial image $AI_1$ that is used for planning the insertion route I and the currently displayed axial image $AI_2$ are not identical. However, the operator can easily grasp the positional relation between the axial image $AI_1$ (the image with the insertion route I set) and the currently displayed axial image $AI_2$ as the deviation between the axial images can be confirmed from the viewing box V. In this case, based on the input of instructions through the input device, etc., the rendering processing part 41c can change the direction of rendering such that the cross-sectional position c' coincides with the cross-sectional position C'.

Further, the display controller 44 can additionally display a mark (an arrow, etc., not illustrated) indicating the rendering direction of the second volume data in the viewing box V. The operator can easily grasp from which direction the image displayed on the display screen are rendered by confirming this mark.

<Operation>

Figure 11:
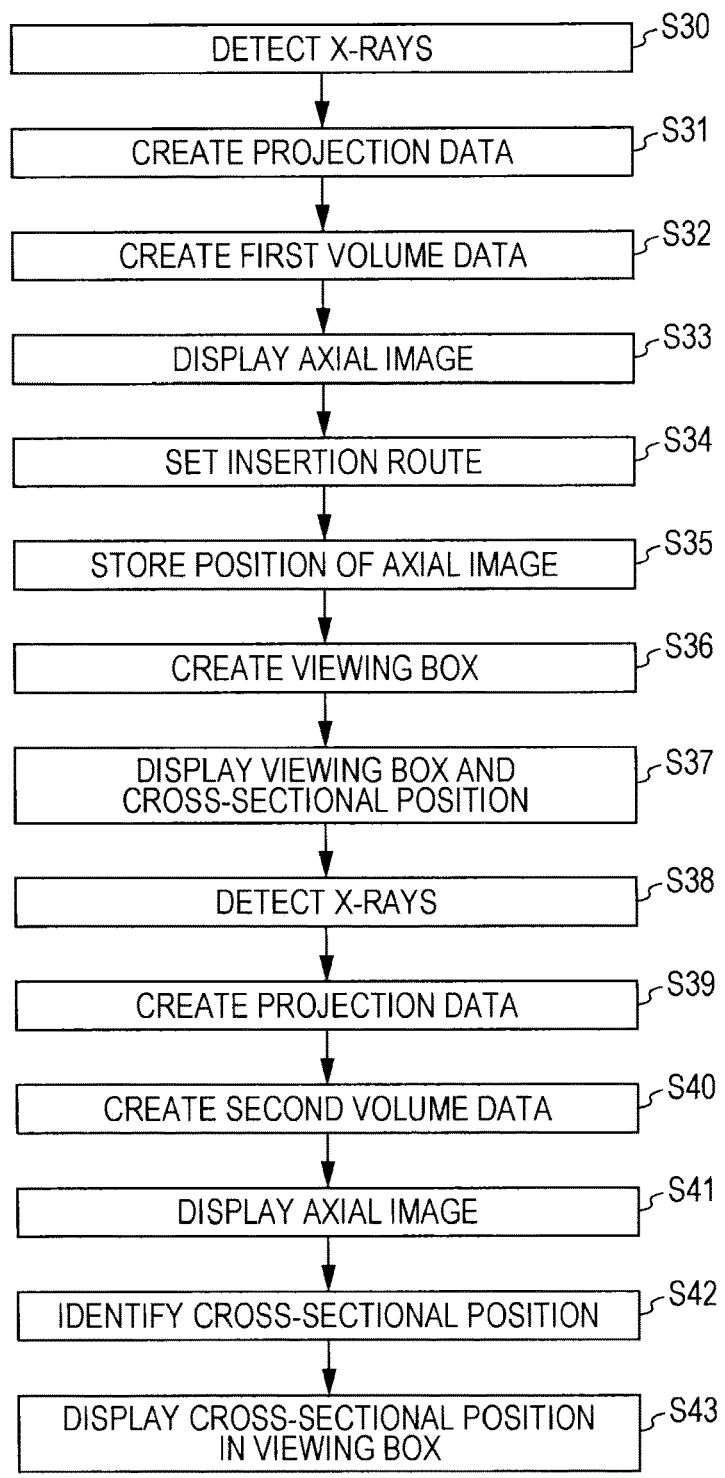
FIG. 11 is a flowchart showing the summary of the operation of the X-ray CT system according to the third embodiment.

Next, the operation of the X-ray CT system 1 according to the present embodiment will be described with reference to FIG. 11. Here, the operation when carrying out a biopsy using CT fluoroscopy after the insertion route I of the puncture needle is created on the axial image $AI_1$ will be described.

Before starting a biopsy, at first, the X-ray CT system 1 creates volume data (first volume data) by carrying out X-ray scanning (first scan) on the subject E.

Specifically, the X-ray generator 11 radiates X-rays onto the subject E. The X-ray detector 12 detects the X-rays transmitted through the subject E, and acquires the detected data (S30). The preprocessing part 41a carries out preprocessing such as logarithmic conversion processing, offset correction, sensitivity correction, and beam hardening correction on the detected data obtained in S30 and creates projection data (S31). The reconstruction processing part 41b creates a plurality of cross-sectional image data based on the projection data created in S31. In addition, the reconstruction processing part 41b creates first volume data by interpolating the plurality of cross-sectional image data (S32).

The rendering processing part 41c creates an axial image $AI_1$ by rendering the first volume data created in S32. The display controller 44 displays the created axial image $AI_1$ on the display 45 (S33).

The operator creates a plan (a planned route) for the insertion route I of the puncture needle by referring to the axial image $AI_1$ displayed on the display 45. The operator designates the position of lesions in the axial image $AI_1$, and the insertion position of the puncture needle using an input device, etc. The setting part 42 sets a line segment connecting the designated positions as the insertion route I (S34). The setting part 42 transmits the position C of the axial image $AI_1$ with the insertion route I set in the first volume data to the storage 46. The storage 46 stores the position C of the axial image $AI_1$ (S35).

In addition, the creating part 43 creates a viewing box V by converting the first volume data created in S32 into the predetermined scale size (S36).

Figure 10A:
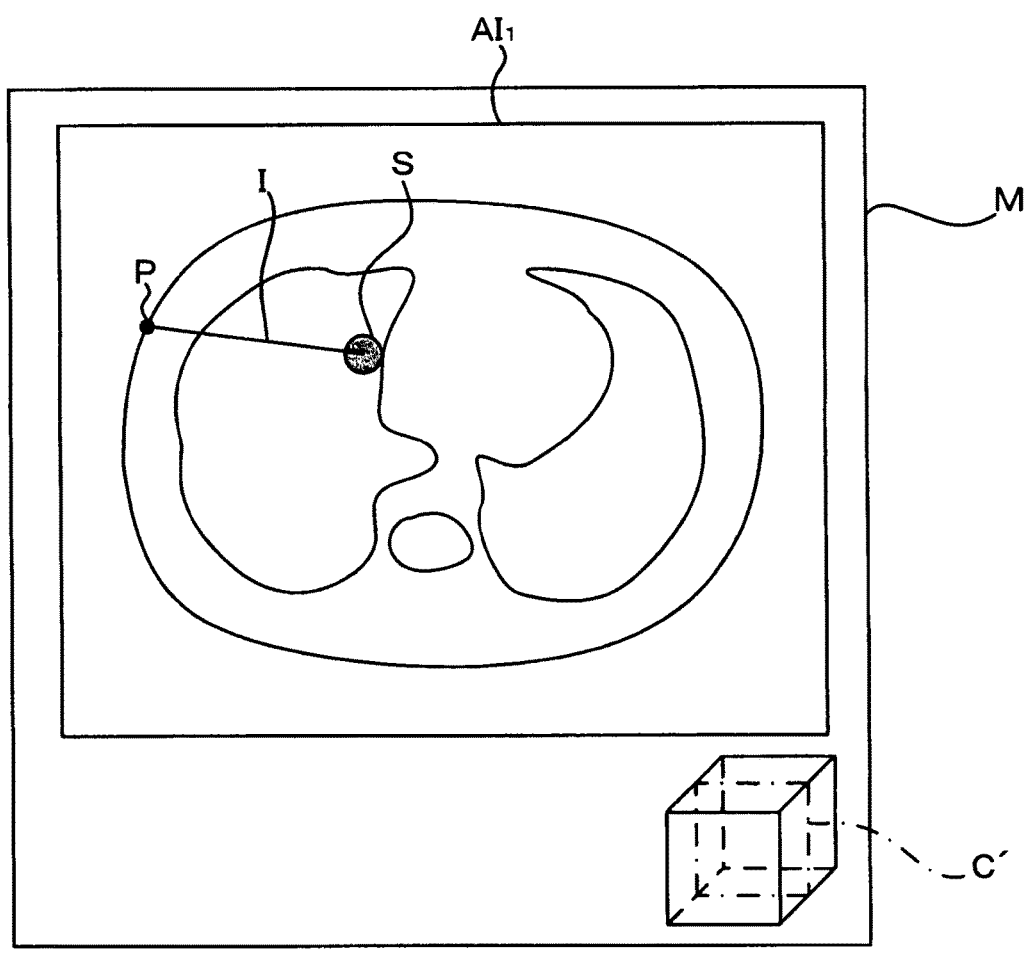
FIG. 10A is a diagram supplementing the explanation of the display controller according to the third embodiment.

The display controller 44 displays the viewing box V created in S36 on the display 45, and displays the cross-sectional position C' corresponding to the position C of the axial image $AI_1$ stored in S35 on the viewing box V (S37; refer to FIG. 10A).

Subsequently, the operator proceeds with puncturing the subject E by referring to the axial image $AI_1$ with the insertion route I indicated and the viewing box V.

After the operator progresses with the biopsy to some extent (after the puncture needle is inserted into the subject E to some extent), the X-ray CT system 1 creates volume data (second volume data) by carrying out X-ray scanning (second scan) on the subject E again in order to confirm the status of puncturing (whether or not the puncture needle is travelling along a planned route, etc.).

In other words, in the same way as the first scan, the X-ray generator 11 radiates X-rays onto the subject E. The X-ray detector 12 detects the X-rays transmitted through the subject E, and acquires the detected data (S38). It is assumed that the imaging conditions, etc. of the first scan and the second scan are identical.

The preprocessing part 41a carries out preprocessing on the detected data obtained in S38, and creates projection data (S39). The reconstruction processing part 41b creates second volume data by interpolating a plurality of cross-sectional image data created based on the projection data created in S39 (S40). The rendering processing part 41c creates an axial image $AI_2$ by rendering the second volume data. The display controller 44 displays the created axial image $AI_2$ on the display 45 (S41; refer to FIG. 10B).

The display controller 44 identifies the cross-sectional position c' corresponding to the position c of the axial image $AI_2$ in the second volume data (S42).

Figure 10B:
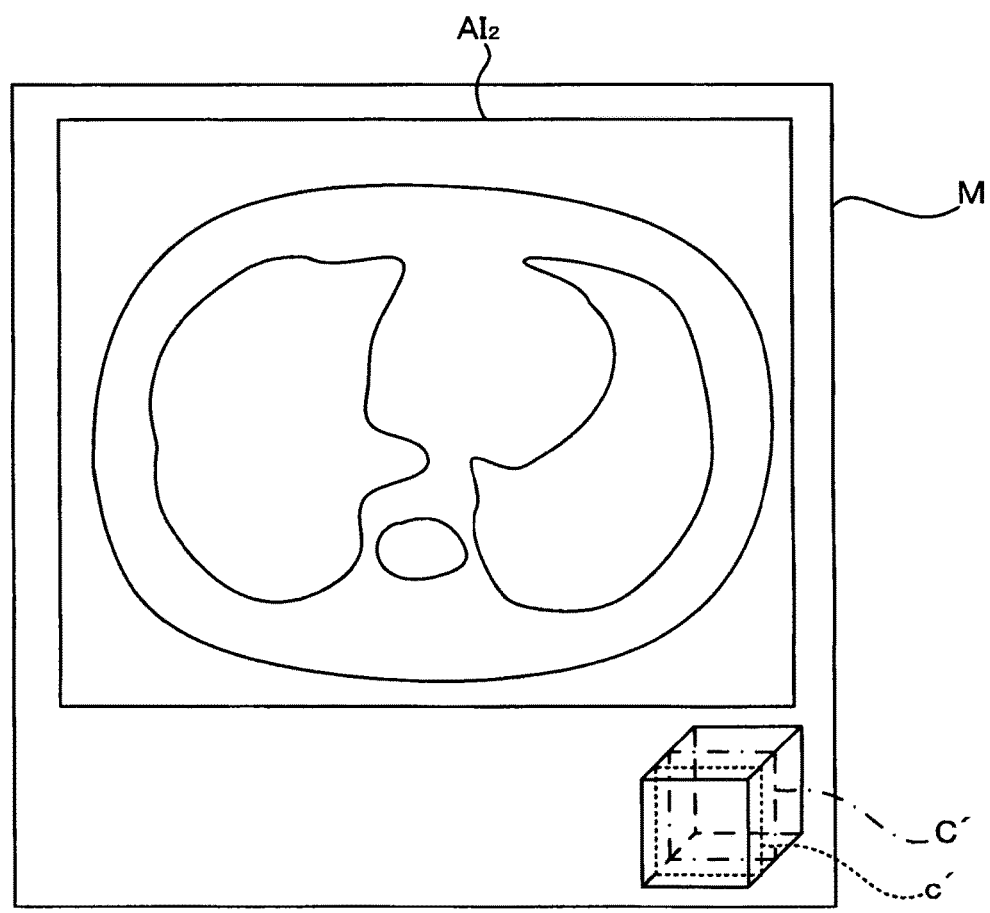
FIG. 10B is a diagram supplementing the explanation of the display controller according to the third embodiment.

The display controller 44 displays the viewing box V created in S36 on the display 45, and displays the cross-sectional position c' identified in S42 on the viewing box V (S43; refer to FIG. 10B).

The display controller 44 can also simultaneously display an axial image, a sagittal image, and a coronal image on the display screen, in addition to being able to display cross-sectional positions corresponding to respective images on the viewing box.

Figure 12:
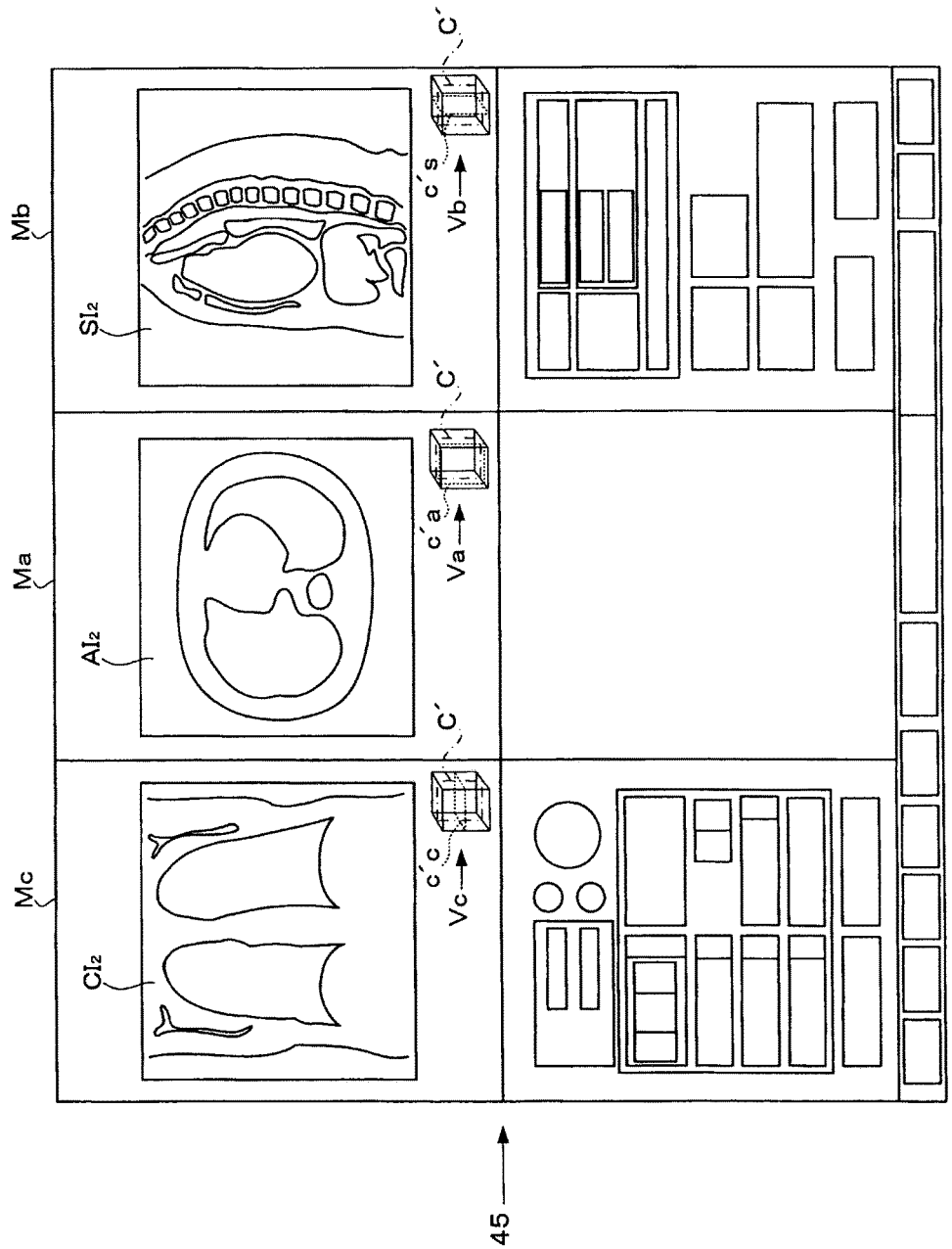
FIG. 12 is a diagram supplementing the explanation of the display controller according to the third embodiment.

FIG. 12 illustrates the display screen of the display 45. An axial image $AI_2$, a sagittal image $SI_2$, and a coronal image $CI_2$ based on the second volume data are displayed on display screens Ma to Mc, respectively. The cross-sectional position C' corresponding to the position C of the MPR images (here, the axial image $AI_1$) with the insertion route I set is displayed on viewing boxes Va to Vc. In addition, a cross-sectional position c'a corresponding to the position of the currently displayed axial image $AI_2$, a cross-sectional position c'c corresponding to the position of the coronal image $CI_2$, and a cross-sectional position c's corresponding to the position of the sagittal image $SI_2$ are displayed on the viewing boxes Va to Vc, respectively.

<Operation and Effect>

The operation and effect of the present embodiment will be described.

The display controller 44 of the X-ray CT system 1 in the present embodiment displays the cross-sectional position c' corresponding to an MPR image based on other volume data (second volume data) different from the first volume data on a graphic (viewing box V).

Specifically, the display controller 44 displays the MPR image based on other volume data (second volume data) on the display 45.

Thus, the display controller 44 displays the cross-sectional position c' corresponding to the MPR image based on the volume data obtained at a certain timing on the viewing box V on which the cross-sectional position C' (or the route images I') corresponding to the MPR images with the insertion route I set is displayed. Thereby, the operator can easily grasp the positional relation between the cross-section (or the planned insertion route I) with the insertion route I planned and the currently display MPR image (the MPR image based on other volume data) in the viewing box V. In other words, the X-ray CT system 1 in the present embodiment can present the information regarding the puncture plan.

Fourth Embodiment

Figure 14:
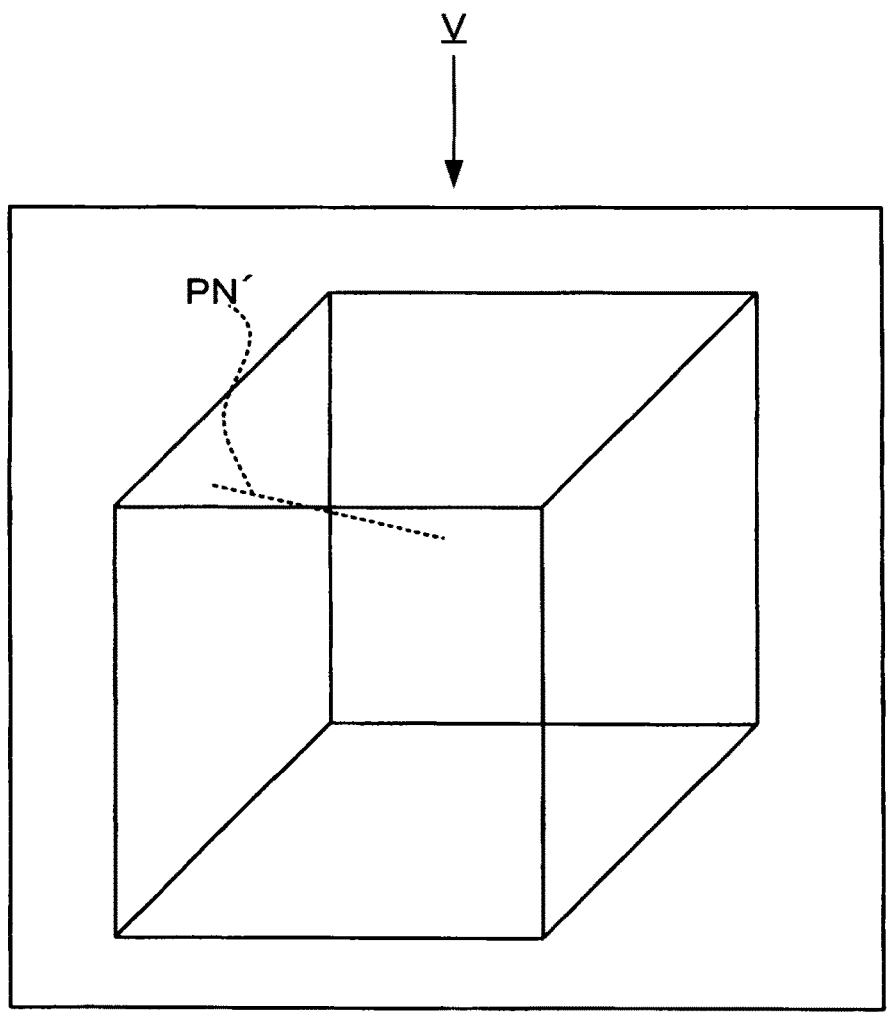
FIG. 14 is a diagram supplementing the explanation of a display controller according to the fourth embodiment.
Figure 15:
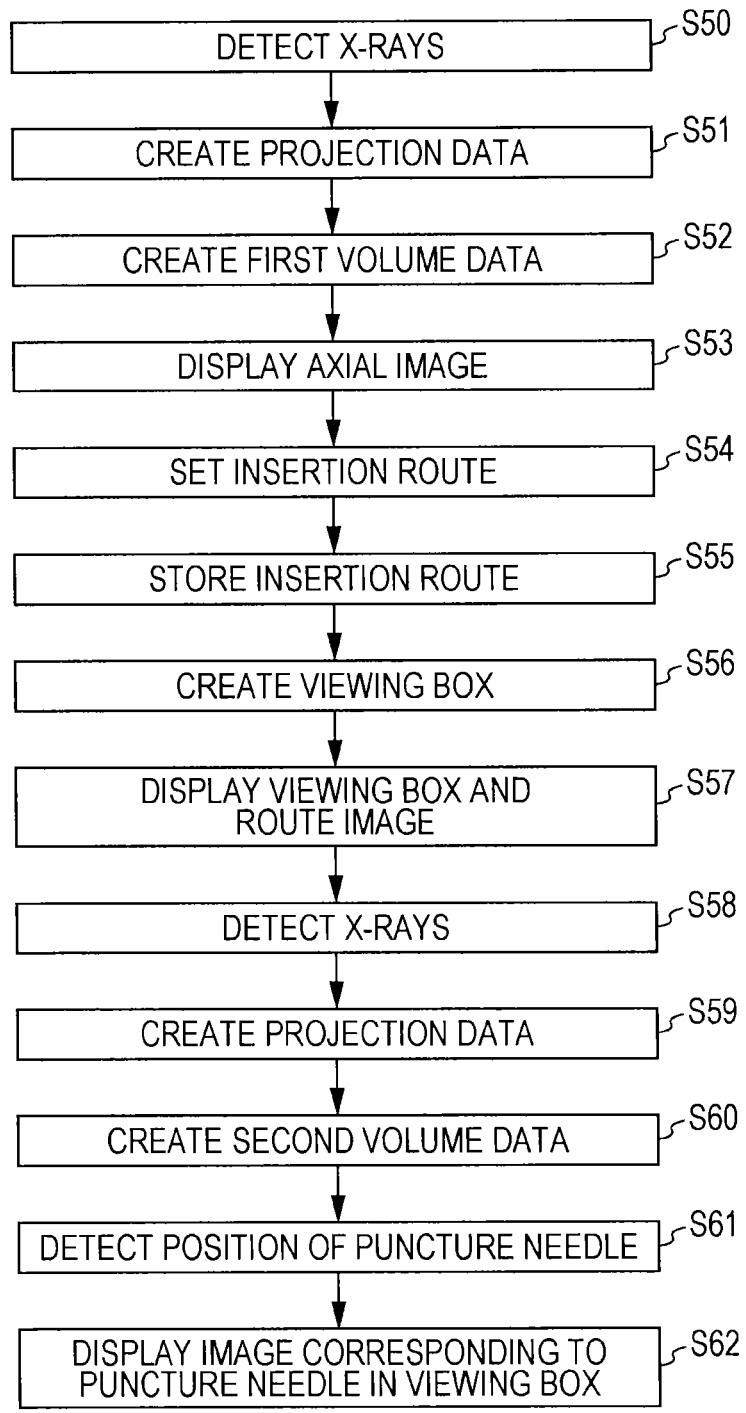
FIG. 15 is a flowchart showing the summary of the operation of the X-ray CT system according to the fourth embodiment.

The configuration of the X-ray CT system 1 (an example of a medical apparatus) according to the fourth embodiment will be described with reference to FIGS. 13 to 15. In the present embodiment, the configuration wherein an image corresponding to a puncture needle PN is displayed on the viewing box V will be described. With respect to configuration identical with the above-described embodiments, a detailed explanation thereof is omitted.

Figure 13:
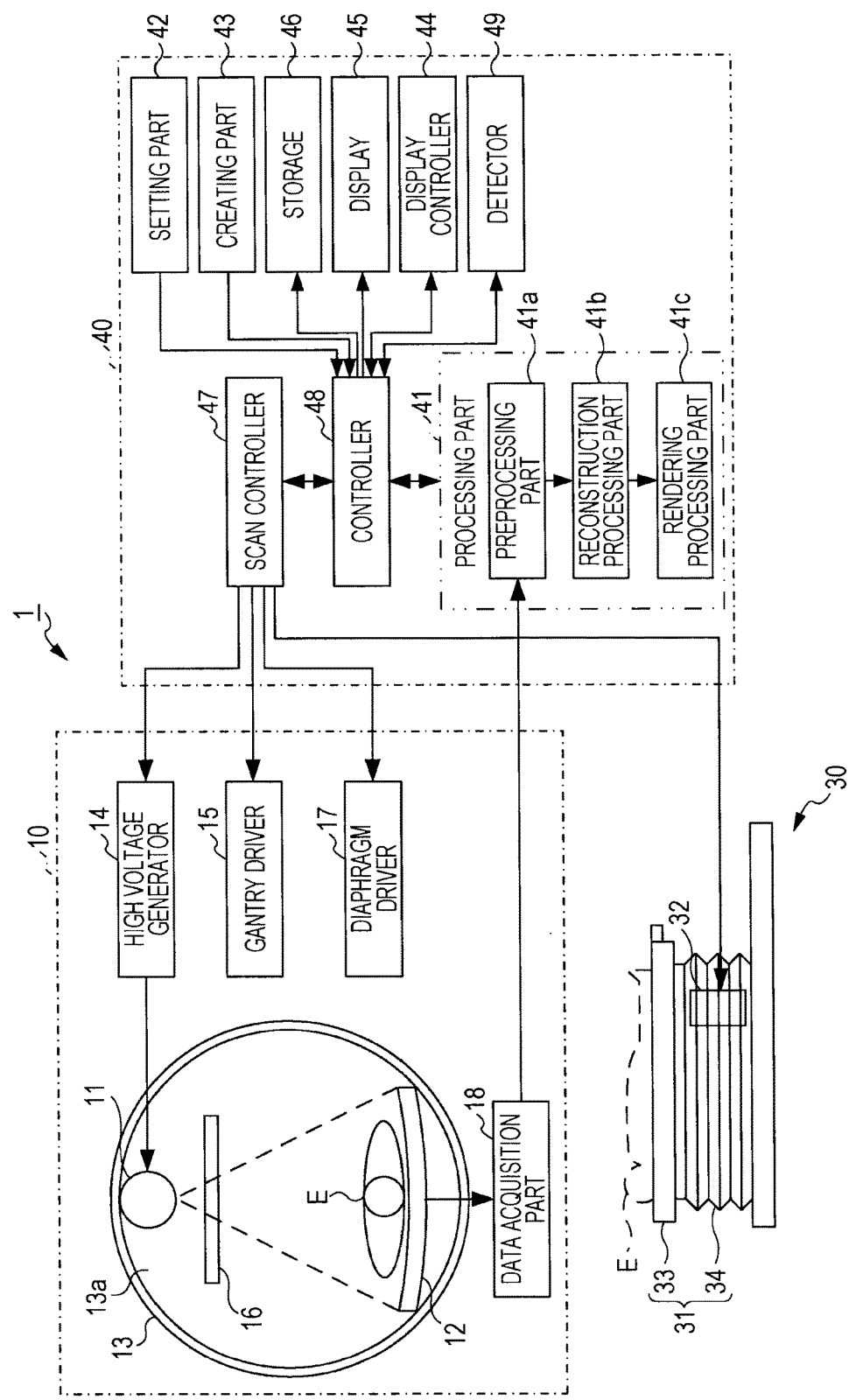
FIG. 13 is a block diagram of the X-ray CT system according to the fourth embodiment.

As illustrated in FIG. 13, the X-ray CT system 1 in the present embodiment has a detector 49. The detector 49 detects the puncture needle PN inserted into the subject E based on other volume data (second volume data) created based on scanning (second scan) at a different timing from that of the first scan. Further, it is assumed that the subject E has already been punctured with the puncture needle PN at the stage of obtaining the second volume data.

For example, the detector 49 detects a voxel having CT values corresponding to the CT values of the puncture needle PN from the second volume data, thereby detects the position of this voxel as the position of the puncture needle PN (coordinate values).

The display controller 44 creates an image PN' corresponding to the puncture needle PN by converting the position (coordinate values) of the detected puncture needle PN into the same scale size as that when creating the viewing box V. The display controller 44 displays the created image PN' on the viewing box V (refer to FIG. 14; FIG. 14 illustrates the viewing box V displayed on the display 45).

<Operation>

Next, the operation of the X-ray CT system 1 according to the present embodiment will be described with reference to FIG. 15. Here, the operation when carrying out a biopsy using CT fluoroscopy after the insertion route I of the puncture needle is created on the axial image $AI_1$ will be described.

Before starting a biopsy, at first, the X-ray CT system 1 creates volume data (first volume data) by carrying out the X-ray scanning (first scan) on the subject E.

Specifically, the X-ray generator 11 radiates X-rays onto the subject E. The X-ray detector 12 detects the X-rays transmitted through the subject E, and acquires the detected data (S50). The preprocessing part 41a carries out preprocessing such as logarithmic conversion processing, offset correction, sensitivity correction, and beam hardening correction on the detected data acquired in S50 and creates projection data (S51). The reconstruction processing part 41b creates a plurality of cross-sectional image data based on the projection data created in S51. In addition, the reconstruction processing part 41b creates first volume data by interpolating the plurality of cross-sectional image data (S52).

The rendering processing part 41c creates an axial image $AI_1$ by rendering the first volume data created in S52. The display controller 44 displays the created axial image $AI_1$ on the display 45 (S53).

The operator makes a plan for the insertion route I by referring to the axial image $AI_1$ displayed on the display 45. The operator designates the position of lesions in the axial image $AI_1$, and the insertion position of the puncture needle using the input device, etc. The setting part 42 sets a line segment connecting the designated positions as the insertion route I (S54). The setting part 42 transmits the coordinate values of the insertion route I to the storage 46. The storage 46 stores the insertion route I (coordinate values) (S55).

In addition, the creating part 43 creates a viewing box V by converting the first volume data created in S52 into the predetermined scale size (S56).

The display controller 44 displays the viewing box V created in S56 on the display 45, and displays a route image I' corresponding to the insertion route I at the corresponding position of the viewing box V (S57).

Subsequently, the operator proceeds with puncturing on the subject E by referring to the axial image $AI_1$ and the viewing box V with the insertion route I indicated.

Once the operator progresses with the biopsy to some extent (after the puncture needle is inserted into the subject E to some extent), the X-ray CT system 1 creates volume data (second volume data) by carrying out the X-ray scanning (second scan) on the subject E again in order to confirm the status of puncturing (whether or not the puncture needle is travelling along a planned route, etc.).

In other words, in the same way as the first scan, the X-ray generator 11 radiates X-rays onto the subject E. The X-ray detector 12 detects the X-rays transmitted through the subject E, and acquires the detected data (S58). It is assumed that the imaging conditions, etc. of the first scan and the second scan are identical.

The preprocessing part 41a carries out preprocessing on the detected data acquired in S38, and creates projection data (S59). The reconstruction processing part 41b creates second volume data by interpolating a plurality of cross-sectional image data created based on the projection data created in S59 (S60).

The detector 49 detects the position of the puncture needle PN based on the second volume data created in S60 (S61).

The display controller 44 displays the image PN' corresponding to the puncture needle PN detected in S61 on the viewing box V displayed in S57 (S62).

In the present embodiment, the configuration such that the route image and the image PN+ are displayed in the viewing box V is described; however, the images displayed in the viewing box V are not limited to this combination. For example, the display controller 44 can display only the image PN' in the viewing box V (in this case, the insertion route I may not be set). Alternatively, the display controller 44 can also display the cross-sectional position C' in the second embodiment and/or the cross-sectional position c' in the third embodiment in the viewing box V together with the image PN'.

<Operation and Effect>

The operation and effect of the present embodiment will be described.

The X-ray CT system 1 of the present embodiment has a detector 49. The detector 49 detects the puncture needle PN inserted into the subject E based on other volume data (second volume data). The display controller 44 displays the image corresponding to the puncture needle PN on the graphic (viewing box V).

Thus, the display controller 44 displays the image PN' corresponding to the puncture needle PN detected based on the other volume data in the viewing box V. Thereby, the operator can easily grasp the position of the puncture needle PN in the viewing box V. In addition, when the route image I' is displayed in the viewing box V, by comparing the route image I' with the image PN', it is possible to easily grasp whether or not puncturing is progressing as planned (when puncturing is progressing as planned, the route image I' and the image PN' are displayed overlapping in the viewing box V). In other words, according to the X-ray CT system 1 in the present embodiment, it is possible to compare the information regarding the presented puncture plan with the actual status of the puncturing.

Modified Example 1

In the above-described embodiments, an example of creating a viewing box based on the shapes of the volume data such that the respective sides have identical scale sizes is described.

Here, for a viewing box of a rectangular parallelepiped as illustrated in FIG. 4, it is necessary to ensure a wider display region in the display 45 as compared to a viewing box of a cube. As a result, it is possible that the viewing box of the rectangular parallelepiped may not be displayed on the display screen due to restrictions of the display regions, etc.

Therefore, the creating part 43 creates a viewing box based on the shape of the volume data such that the respective sides have different scale sizes.

Figure 16:
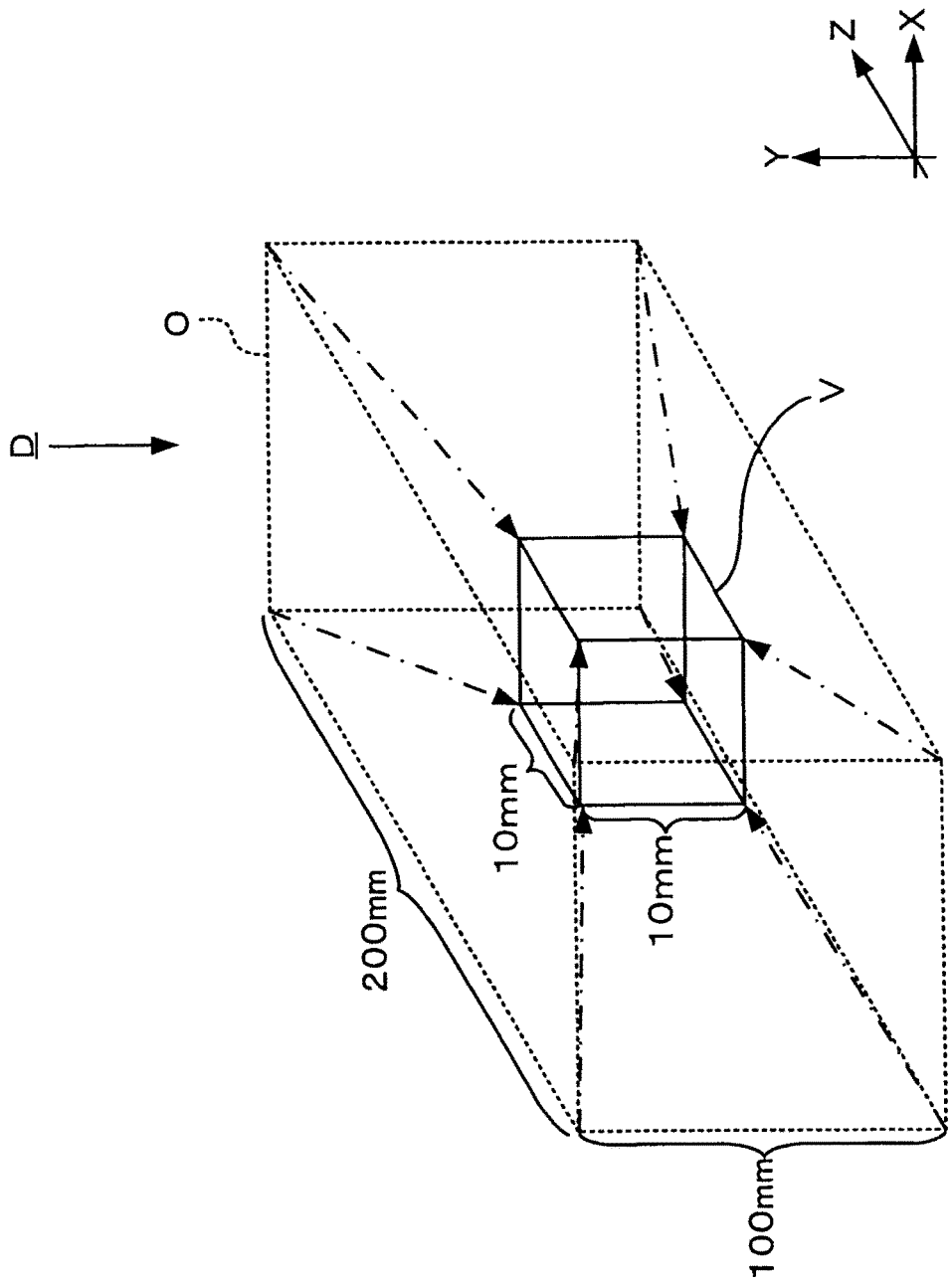
FIG. 16 is a diagram supplementing the explanation of the creating part according to Modified Example 1.

In other words, when the volume data D of the rectangular parallelepiped is acquired, the creating part 43 creates a viewing box V such that it becomes a cube by changing the scale sizes of the XY directions and that of the Z direction orthogonal to the XY directions. For example, as illustrated in FIG. 16, when volume data D (the outline part O) is acquired in which the lengths of the sides in the X direction and the Y direction are 100 mm and the lengths of the sides in the Z direction are 200 mm, the creating part 43 creates a viewing box V such that the lengths of the sides in the X direction, the Y direction, and the Z direction are equal (10 mm) based on the scale sizes in the X direction and the Y direction (for example, 1/10) and a different scale size in the Z direction (for example, 1/20) that have been set in advance.

Modified Example 2

After displaying a viewing box V created at a certain scale size, the display controller 44 can change its scale size. In this case, the display controller 44 also changes the scale size of the route image I', etc. in the viewing box V based on the new scale size.

In addition, the display controller 44 can change the display aspect of a viewing box V (absence or presence of the display, switching of flashing and lighting, change in colors, etc.). Furthermore, the display controller 44 can change only the display aspect (absence or presence of the display, switching of flashing and lighting, change in colors, etc.) of the route image I' and/or the cross-sectional position C' with the viewing box V displayed.

Modified Example 3

The display controller 44 can display an image corresponding to an object site on which a biopsy is carried out in the viewing box V.

Figure 17:
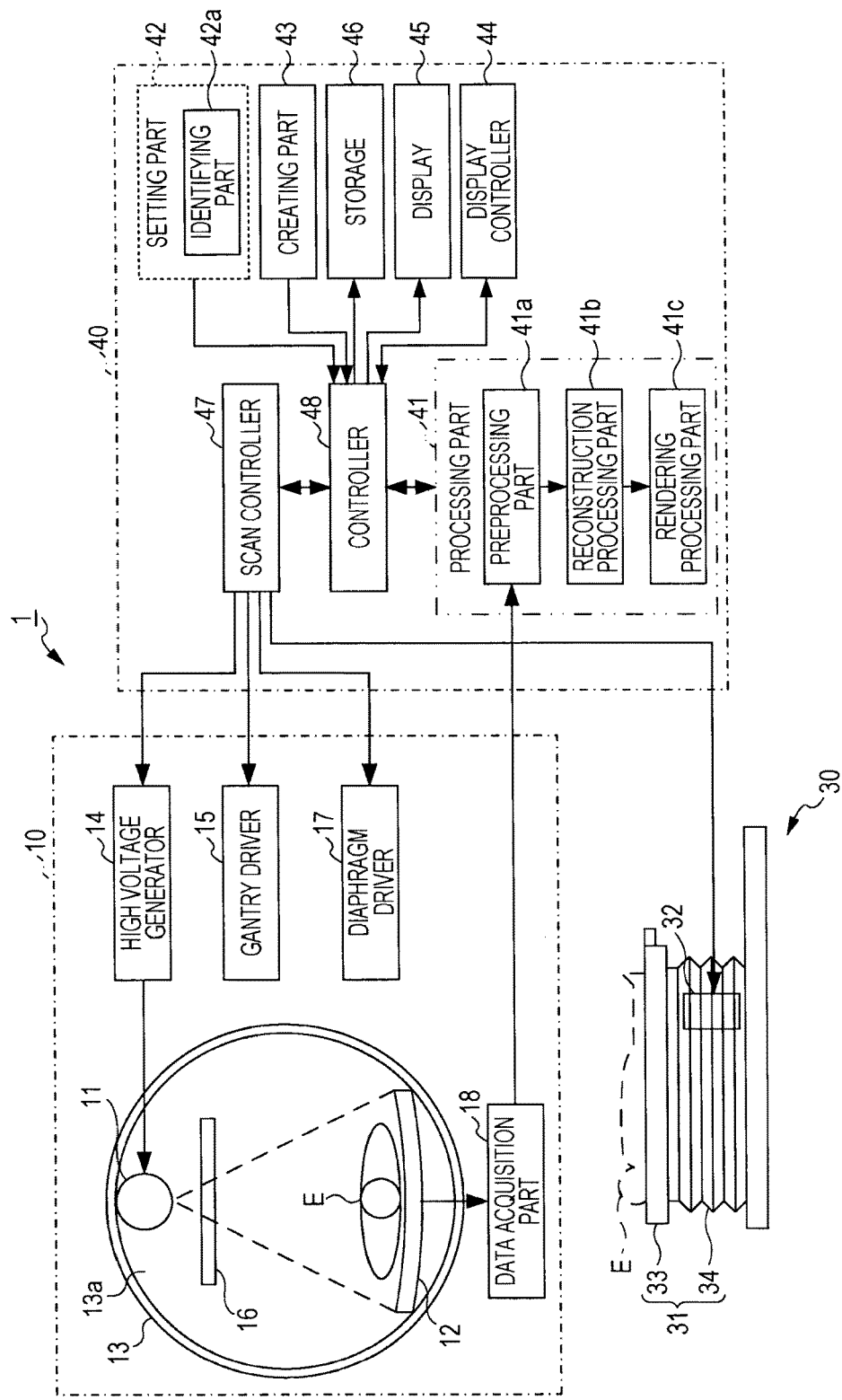
FIG. 17 is a block diagram of the X-ray CT system according to Modified Example 3.

In the present modified example, the setting part 42 comprises an identifying part 42a (refer to FIG. 17). The identifying part 42a identifies an object site on which a biopsy is carried out based on the volume data. Specifically, the identifying part 42a detects a voxel having the CT value corresponding to the CT value of the object site (for example, a lesion) from the volume data, thereby identifies the position of the voxel as the position of the object site (three-dimensional coordinate values).

Further, identification of the object site can be made by analyzing an MPR image based on the volume data. For example, the identifying part 42a obtains the position (coordinate value) of the object site in the X direction and the Y direction by carrying out a method such as edge detection on the axial image including the object site. In addition, this axial image is an image based on the volume data. Accordingly, the identifying part 42a derives the position (coordinate value) of the object site in the Z direction based on the volume data.

Figure 18:
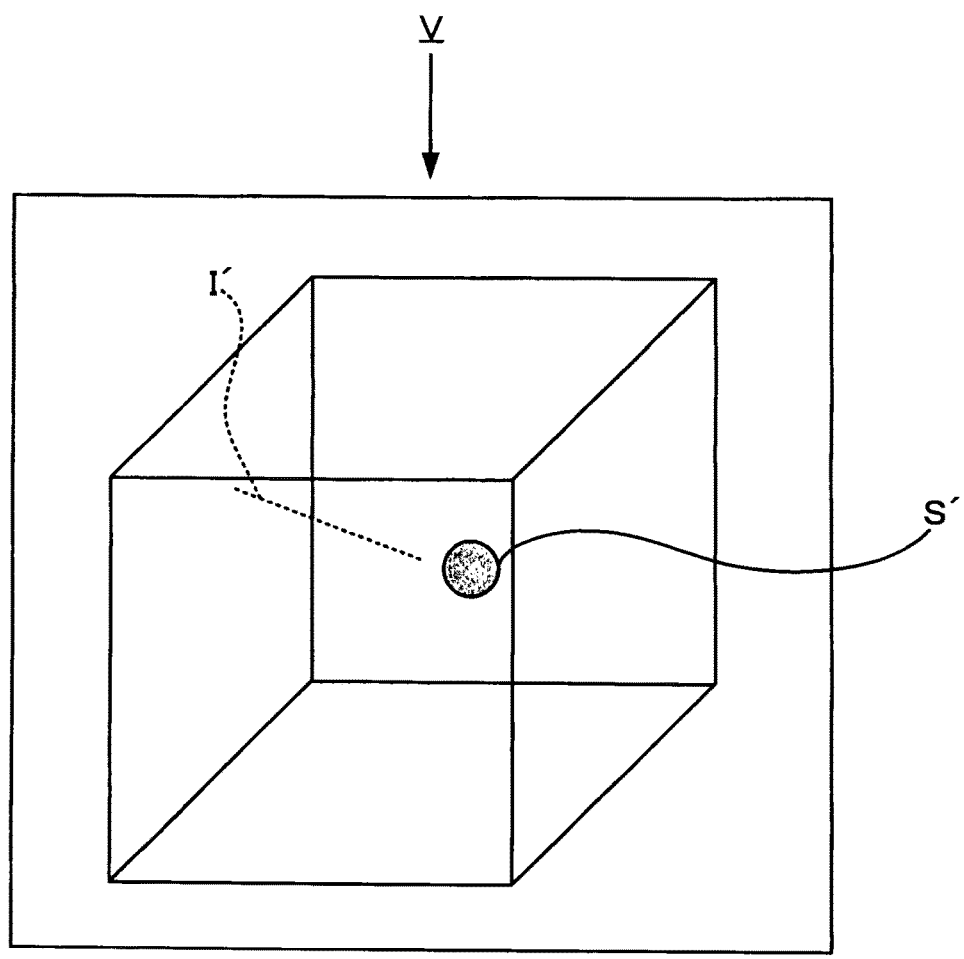
FIG. 18 is a diagram supplementing the explanation of the display controller according to the Modified Example 3.

The display controller 44 creates an image S' corresponding to the object site by converting the position (three-dimensional coordinate values) of the object site into the same scale size as that when creating the viewing box V. The display controller 44 displays the created imag S' in the viewing box V (refer to FIG. 18). FIG. 18 illustrates the viewing box V displayed on the display 45. In addition, FIG. 18 illustrates an example of displaying the route image I' together with the image S'.

Thus, by displaying the image corresponding to the object site in the viewing box V and combining the image with the above-described respective embodiments, it becomes possible to easily grasp the puncture plan and the positional relation between the puncture needle actually inserted and the object site in the viewing box V.

Modified Example 4

In the above-described examples, the X-ray CT system 1 is described as an example; however, the configuration of the above-described embodiment also can be applied to an ultrasound diagnosis apparatus. In other words, an ultrasound diagnosis apparatus is an example of a medical apparatus. For example, an ultrasound diagnosis apparatus creates volume data by sending and receiving ultrasound waves to and from the subject E in a fan-shape. In this case, the creating part 43 creates a graphic in a fan-shape schematically indicating the volume data as the above-mentioned graphic (viewing box V). In other words, the shape of the graphic created by the creating part 43 corresponds to the shape of the volume data.

Effects Common to the First to Fourth Embodiments

According to a medical apparatus of at least one of the above-described embodiments, the display controller displays the viewing box on the display, and displays the information regarding the puncture plan in the viewing box V. In other words, the medical apparatus can present the information regarding the puncture plan.

Fifth Embodiment

In order to ensure puncturing of the subject, there is a request that an operator wants to confirm the set insertion route from various directions.

In order to satisfy the above-described request, the object of the embodiment is to provide an X-ray CT system capable of displaying an image that can easily confirm the insertion route of the puncture needle.

The configuration of the X-ray CT system 1 according to the fifth embodiment will be described with reference to FIGS. 19 to 23. Further, as "image" and "image data" correspond to each other in one-to-one fashion, sometimes these are used interchangeably in the present embodiment. In addition, in the present embodiment, an explanation will be provided with the body axial direction of a subject E defined as the Z direction (slice direction), the lateral direction orthogonal to the body axial direction defined as the X direction (channel direction), and the lengthwise direction as the Y direction.
<Configuration of the Apparatus>

Figure 19:
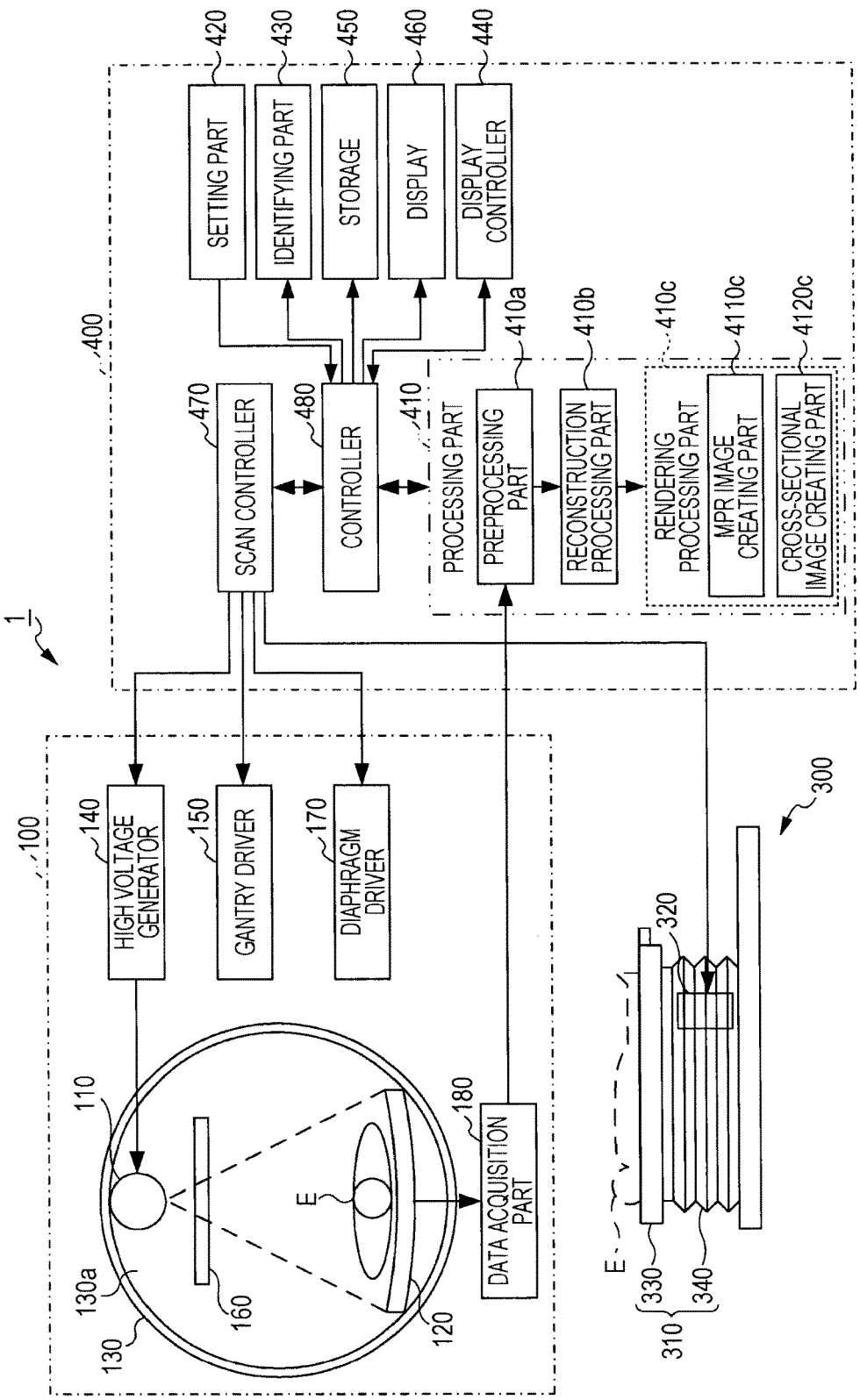
FIG. 19 is a block diagram of the X-ray CT system according to the fifth embodiment.

As illustrated in FIG. 19, the X-ray CT system 1 comprises a gantry device 100, a bed device 300, and a console device 400.
[Gantry Device]

The gantry device 100 is a device that radiates X-rays onto the subject E and acquires the detected data from these X-rays transmitted through the subject E. The gantry device 100 comprises an X-ray generator 110, an X-ray detector 120, a rotational body 130, a high voltage generator 140, a gantry driver 150, an X-ray diaphragm part 160, a diaphragm driver 170, and a data acquisition part 180.

The X-ray generator 110 comprises an X-ray tube that generates X-rays (for example, a vacuum bulb to generate X-ray beams in a conical or pyramid-like shape, not illustrated). The X-ray generator 110 radiates the generated X-rays onto the subject E.

The X-ray detector 120 comprises a plurality of X-ray detection elements (not illustrated). The X-ray detector 120 detects the X-rays transmitted through the subject E. Specifically, the X-ray detector 120 detects X-ray intensity distribution data indicating the intensity distribution of X-rays transmitted through the subject E by means of an X-ray detection element, then, outputs the detected data as a current signal. As the X-ray detector 120, for example, a two-dimensional X-ray detector (plane detector) is used in which a plurality of detection elements are respectively arranged in two directions (slice direction and channel direction) orthogonal to each other. For example, a plurality of X-ray detection elements is arranged in 320 rows along the slice direction. Thereby, using the X-ray detectors in a plurality of rows, due to a 360-degree scanning roll, a three-dimensional imaging region having a width in the slice direction can be imaged (a volume scan). Further, the slice direction corresponds to the body axial direction of the subject E, while the channel direction corresponds to the rotational direction of the X-ray generator 110.

The rotational body 130 is a member that supports the X-ray generator 110 and the X-ray detector 120 such that they are opposed across the subject E. The rotational body 130 has an opening 130a penetrating therethrough in the slice direction. In the gantry device 100, the rotational body 130 is arranged such that it rotates in a circular orbit around the subject E. In other words, the X-ray generator 110 and the X-ray detector 120 are arranged so as to be capable of rotating along a circular orbit around the subject E.

The high voltage generator 140 applies a high voltage to the X-ray generator 110. The X-ray generator 110 generates X-rays based on this high voltage.

The gantry driver 150 rotatively drives the rotational body 130. The X-ray diaphragm part 160 has a slit (aperture) of a predetermined width, and adjusts the fan angle (spread angle in the channel direction) of the X-rays and cone angle (spread angle in the slice direction) of the X-rays that are radiated from the X-ray generator 110 by changing the width of the slit. The diaphragm driver 170 drives the X-ray diaphragm part 160 such that the X-rays generated by the X-ray generator 110 are formed into a predetermined shape.

The data acquisition part 180 (DAS) acquires detected data from the X-ray detector 120 (each X-ray detection element). In addition, the data acquisition part 180 converts the acquired detected data (current signals) into voltage signals, amplifies these voltage signals by periodically integrating them, and converts them into digital signals. Then, the data acquisition part 180 transmits the detected data converted into digital signals to the console device 400. Further, in the event of carrying out CT fluoroscopy, it is desirable that, based on the detected data acquired by the data acquisition part 180, a reconstruction processing part 410b (to be described later) carries out reconstruction processing for a short time and obtains the CT images in real time. Accordingly, the data acquisition part 180 shortens the acquisition rate of the detected data.
[Bed Device]

The bed device 300 is a device for mounting and moving the subject E of an imaging object. The bed device 300 is provided with a bed 310 and a bed driver 320. The bed 310 is provided with a bed top board 330 for mounting the subject E thereon and a base 340 for supporting the bed top board 330. The bed top board 330 can be moved by the bed driver 320 in the body axial direction of the subject E and a direction orthogonal to the body axial direction thereof. In other words, the bed driver 320 can insert and pull the bed top board 330 having the subject E mounted thereon into and from an opening 130a of the rotational body 130. The base 340 can move the bed top board 330 vertically (direction orthogonal to the body axial direction of the subject E) using the bed driver 320.

[Console Device]

The console device 400 is used for manipulation and input with respect to the X-ray CT system 1. In addition, the console device 400 has a function, etc. for reconstructing CT image data (cross-sectional image data and volume data) representing the inner morphology of the subject E from the detected data acquired by the gantry device 100. The console device 400 comprises a processing part 410, a setting part 420, an identifying part 430, a display controller 440, a storage 450, a display 460, a scan controller 470, and a controller 480.

The processing part 410, carries out various processing with respect to the detected data transmitted from the gantry device 100 (data acquisition part 180). The processing part 410 comprises a preprocessing part 410a, a reconstruction processing part 410b, and a rendering processing part 410c.

The preprocessing part 410a carries out preprocessing such as logarithmic conversion processing, offset correction, sensitivity correction, and beam hardening correction on the detected data detected by the gantry device 100 (X-ray detector 120), and creates projection data.

The reconstruction processing part 410b creates CT image data (cross-sectional image data and three-dimensional volume data) based on the projection data created in the preprocessing part 410a. In order to reconstruct the cross-sectional image data, any method, for example, a two-dimensional Fourier transformation method, a convolution/back projection method, etc. can be adopted. The volume data is created by interpolating a plurality of reconstructed cross-sectional image data. In order to reconstruct the volume data, for example, any method such as a cone beam reconstruction method, a multi-slice reconstruction method, an enlarged reconstruction method, etc. can be adopted. As described above, due to volume scanning using an X-ray detector in multiple rows, it is possible to reconstruct the volume data over a wide range. In addition, in the event of carrying out CT fluoroscopy, the acquisition rate of the detected data is made shorter and the reconstruction time due to the reconstruction processing part 410b is shortened. Accordingly, CT image data corresponding to the scanning can be created in real time.

The rendering processing part 410c carries out rendering processing on the three-dimensional volume data created by the reconstruction processing part 410b to create pseudo three-dimensional images and MPR images. The "pseudo three-dimensional images" are images for two-dimensionally displaying the three-dimensional configuration of the subject E. The "MPR images" are images indicating the desired cross-section of the subject E. The MPR images include three orthogonal cross-sections, that is, an axial image, a sagittal image and a coronal image, and an oblique image indicating an arbitrary cross-section.

In the present embodiment, the rendering processing part 410c includes an MPR image creating part 4110c and a cross-sectional image creating part 4120c.

The MPR image creating part 4110c creates MPR images indicating cross-sections in a predetermined direction in the volume data. For example, it is assumed that, based on the detected data from the X-ray detection elements of 320 rows (Z direction), the reconstruction processing part 410b creates single volume data. In this case, by carrying out rendering processing on this volume data, the MPR image creating part 4110c can create a plurality of axial images $Ax_k$ (k=1 to 320) as the MPR images indicating cross-sections in a predetermined direction. In addition, the MPR image creating part 4110c can also create sagittal images $Sg_k$ (k=1 to 320) and/or coronal images $Co_k$ (k=1 to 320) as the MPR images indicating cross-sections in a different direction from the predetermined direction.

The cross-sectional image creating part 4120c creates cross-sectional images (oblique images), wherein the cross-sections are orthogonal to the MPR images created by the MPR image creating part 4110c and are in any direction. The cross-sectional image creating part 4120c will be described later in detail.

The setting part 420 is used for setting the insertion route of the puncture needle for the subject E based on the MPR images. The insertion route to be set is a route indicating the route along which the puncture needle is inserted in the subject E.

Figure 20A:
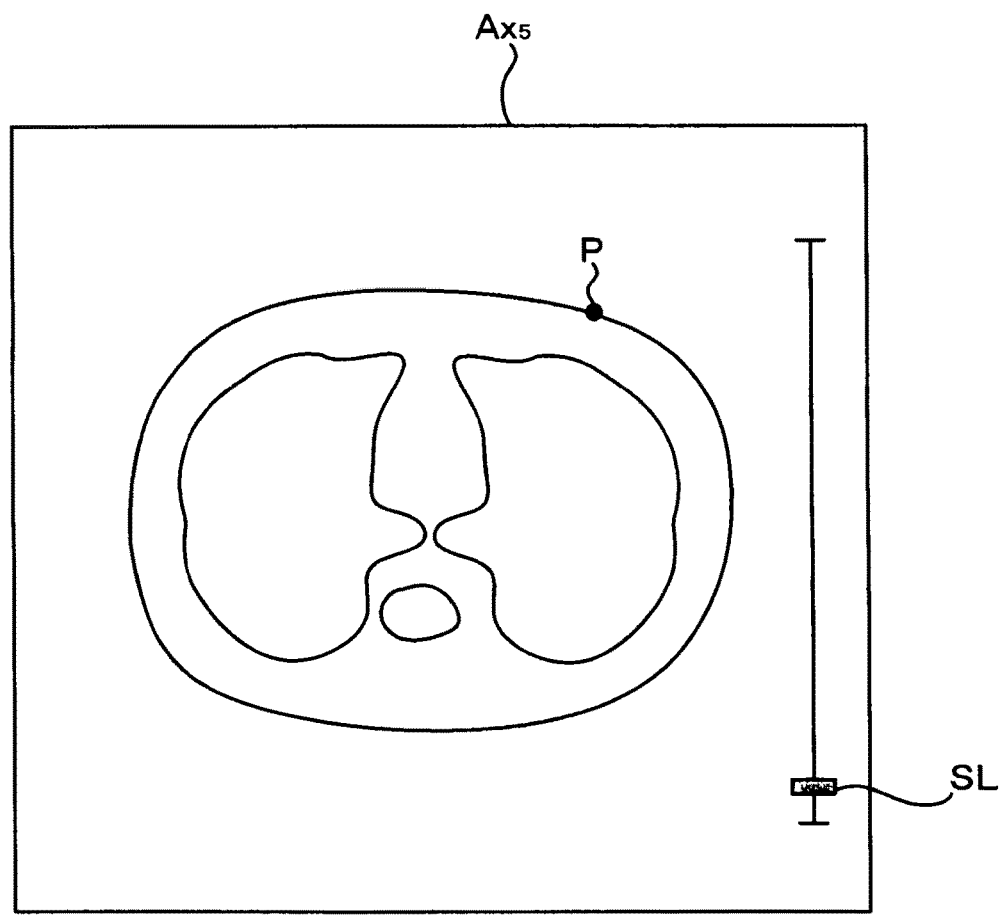
FIG. 20A is a diagram supplementing the explanation of the setting part according to the fifth embodiment.
Figure 20B:
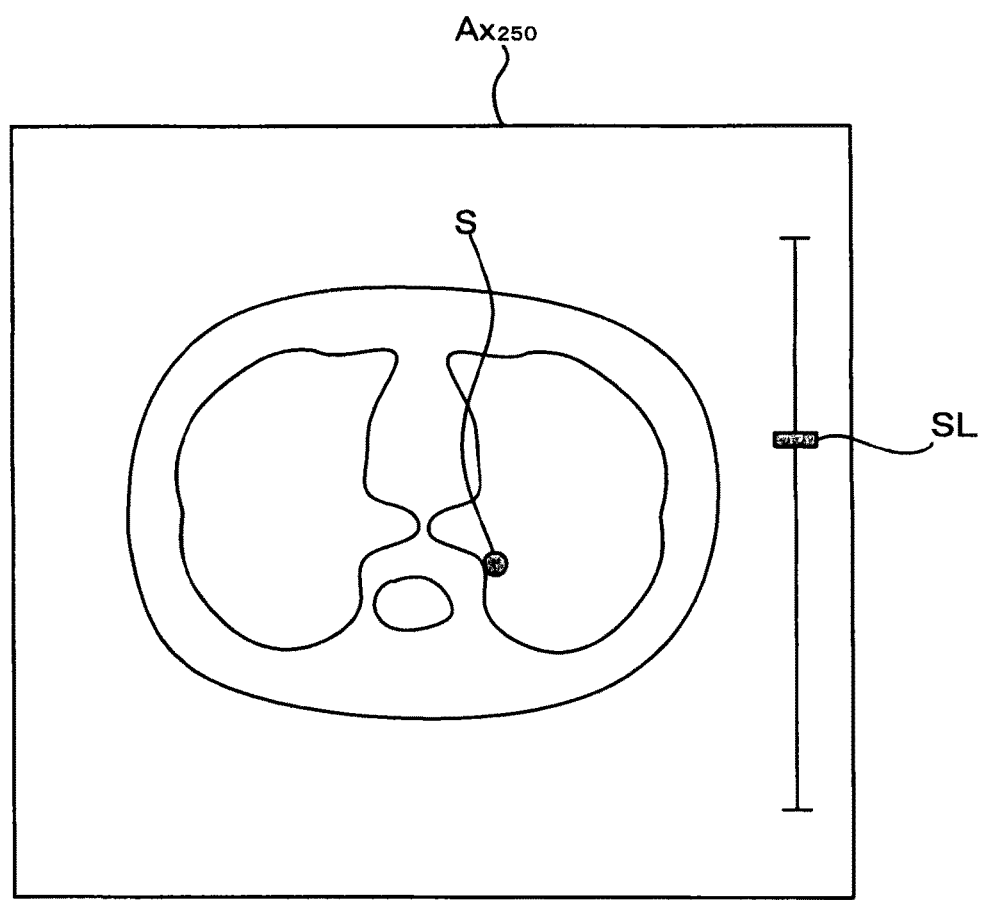
FIG. 20B is a diagram supplementing the explanation of the setting part according to the fifth embodiment.

As a specific example of the setting part 420, the case of setting the insertion route L based on the axial images $Ax_k$ (k=1 to 320) created form the volume data V will be described. FIG. 20A and FIG. 20B illustrate the axial image $Ax_k$ displayed on the display 460. Further, the axial image $Ax_k$ is an image based on the three-dimensional volume data V. Accordingly, the insertion route L (the position of the insertion route) set based on the axial image $Ax_k$ can be identified by the three-dimensional coordinate values.

At first, the operator designates the insertion position P of the puncture needle on the body surface in any axial image (here, the axial image $Ax_5$) displayed on the display 460 using an input device (key board, mouse, etc.) installed in the X-ray CT system 1, etc. (refer to FIG. 20A).

Next, switching the axial images displayed on the display 460 in series using the input device, the operator looks for the axial image (here, the axial image $Ax_{250}$) with the object site (a lesion, etc.) on which the biopsy is carried out displayed. Switching of the images is carried out, for example, by sliding a slide bar SL (refer to FIG. 20A, etc.) displayed on the display screen of the display 460 via the input device.

Figure 20C:
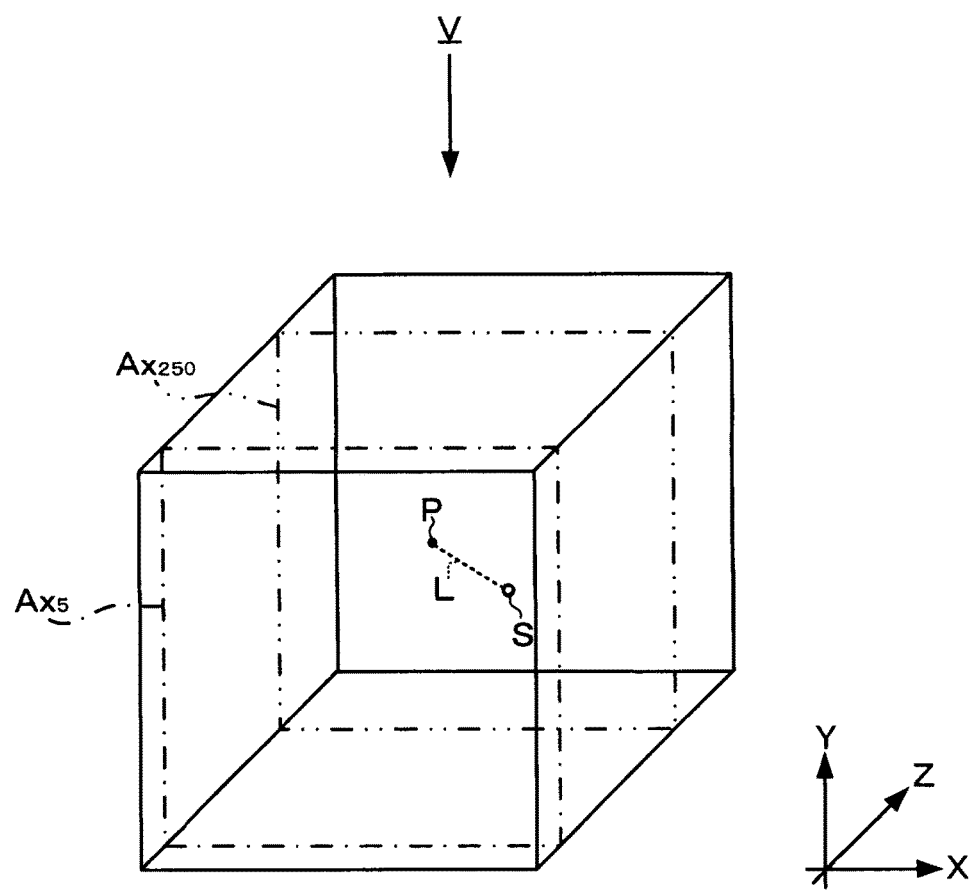
FIG. 20C is a diagram supplementing the explanation of the setting part according to the fifth embodiment.

Once the axial image $Ax_{250}$ with the object site displayed can be identified, the operator designates the position S of the object site using the input device (refer to FIG. 20B). The insertion position P and the position S of the object site are positions in the volume data V. Accordingly, the insertion position P and the position S of the object site can be identified by three-dimensional coordinates. The setting part 420 calculates the shortest distance between these two points and sets a line segment connecting this shortest distance as the insertion route L (refer to FIG. 20C; FIG. 20C is a schematic diagram illustrating the insertion route L in the volume data V). The three-dimensional position (coordinate values) of the insertion route L is stored in the storage 450.

An example of designating the insertion position P first is herein described; however, the position S of the object site can also be designated first. In other words, the operator designates the position S of the object site on the axial image. Then, the operator can designate the insertion position P, while confirming the positions of the site (for example, blood vessels, bones) in which puncturing should be avoided and switching the axial images. Also in this case, the setting part 420 sets a line segment connecting the shortest distance between the designated two points as the insertion route L.

The setting part 420 carries out image processing such as a region-growing method on the MPR images to calculate the position S of the object site. Then, calculating the position on the body surface that is nearest from the object site in the volume data including the MPR images as the insertion position P, the setting part 420 can set a line segment connecting the shortest distance between the position S and the insertion position P as the insertion route L.

In addition, the setting part 420 can set the insertion route L not based on axial images, but rather based on sagittal images, coronal images, or oblique images.

Further, in the above-described specific examples, an example is described in which the insertion route L is set based on a plurality of axial images $Ax_k$; however, in the event of inserting the puncture needle from a parallel direction of the cross-section, it is also possible to set the insertion route L on a single MPR image. MPR images are images based on the volume data. Therefore, even in single MPR images, the setting part 420 can identify the designated insertion position P and the position S of the object site as three-dimensional coordinate values. The setting part 420 sets a line segment connecting the identified two points as the insertion route L.

In the present embodiment, the MPR image (single or a plurality of MPR images) indicating a cross-section in a predetermined direction used for setting the insertion route L corresponds to a "first MPR image," while the MPR image (single or a plurality of MPR images) indicating a cross-section in a different direction from this predetermined direction corresponds to a "second MPR image."

Figure 21:
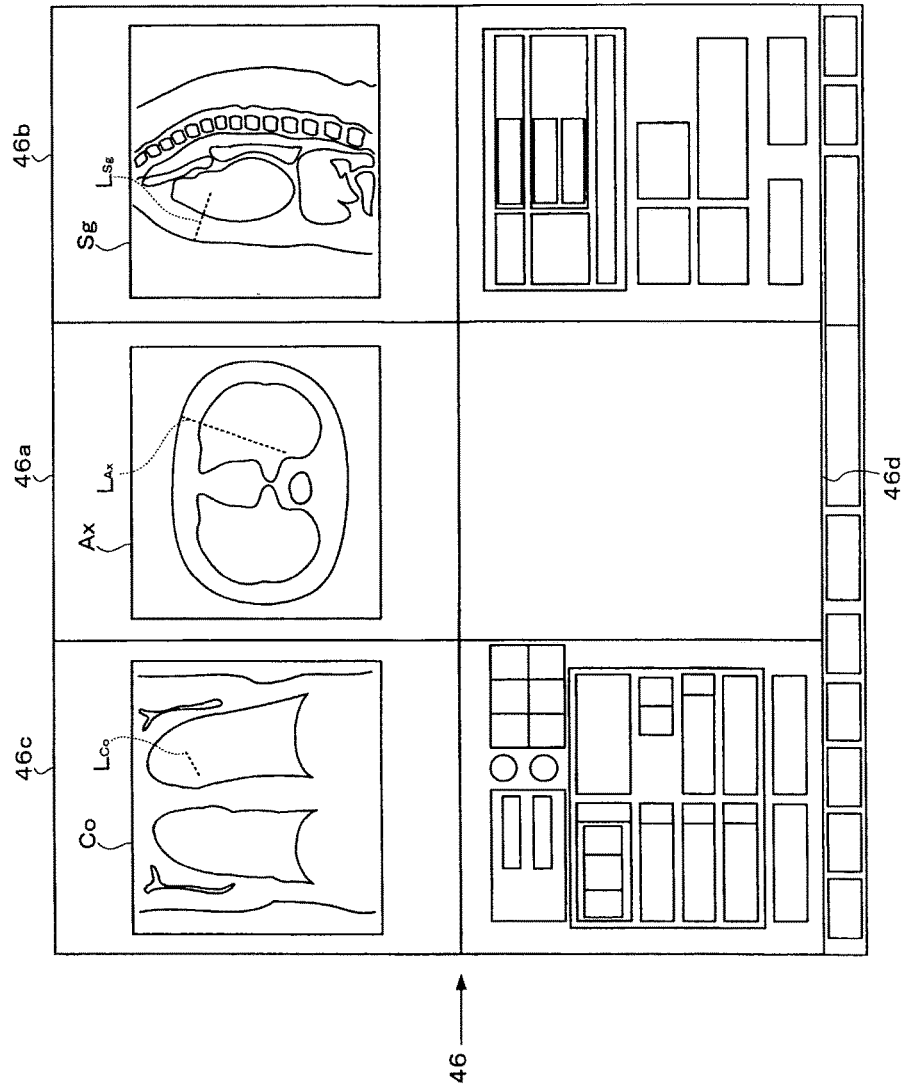
FIG. 21 is a diagram supplementing the explanation of the identifying part according to the fifth embodiment.

The identifying part 430 identifies image regions corresponding to the insertion route in the MPR images (first MPR images and second MPR images). Here, an example of identifying the image regions corresponding to the insertion route L in a single axial image Ax, a single sagittal image Sg, and a single coronal image Co are described. FIG. 21 illustrates an example of the display screen of the display 460. The axial image Ax is displayed on a display screen 460a. The sagittal image Sg is displayed on a display screen 460b. The coronal image Co is displayed on the screen 460c. Further, it is assumed that the axial image Ax, the sagittal image Sg, and the coronal image Co, as well as the axial image $Ax_k$ used upon setting the insertion route L are MPR images based on the identical volume data. In other words, here, the axial image Ax corresponds to one of the axial images $Ax_k$.

As described above, the insertion route can be identified by three-dimensional coordinate values. Accordingly, for the axial image Ax, the sagittal image Sg, and the coronal image Co, the identifying part 430 identifies the positions on the images corresponding to the coordinate values of the insertion route L as image regions $L_{A\_x}$, $L_{S\_g}$, $L_{C\_o}$, respectively. The display controller 440 displays the identified image regions overlapping on respective images (refer to FIG. 21).

Here, the image region $L_{A\_x}$ identified by the axial image Ax only indicates the position (coordinate values) in the XY directions of the set insertion route L. Similarly, the image region $L_{S\_g}$ identified by the sagittal image Sg only indicates the position (coordinate values) in the XZ directions of the set insertion route L. The image region $L_{C\_o}$ identified by the coronal image Co only indicates the position (coordinate values) in the YZ directions of the set insertion route L. In other words, the image regions displayed on respective MPR images schematically illustrate the set insertion route L.

Therefore, for each of the axial image Ax with the image region $L_{A\_x}$ identified, the sagittal image Sg with the image region $L_{S\_g}$ identified, and the coronal image Co with the image region $L_{C\_o}$ identified, the cross-sectional image creating part 4120c creates cross-sectional image of the cross-section orthogonal to the cross-section of the MPR image and along the image region.

Specifically, the cross-sectional image creating part 4120c creates cross-sectional image $O_{A\_x}$ by rendering the volume data in the direction of the cross-section orthogonal to the axial image Ax and along the image region $L_{A\_x}$ on the axial image Ax. Similarly, the cross-sectional image creating part 4120c creates cross-sectional image $O_{S\_g}$ by rendering the volume data in the direction of the cross-section orthogonal to the sagittal image Sg and along the image region $L_{S\_g}$ on the sagittal images Sg. In addition, the cross-sectional image creating part 4120c creates cross-sectional image $O_{C\_o}$ by rendering the volume data in the direction of the cross-section orthogonal to the coronal image Co and along the image region $L_{C\_o}$ on the coronal image Co. The created cross-sectional images are images including the insertion route L. The created cross-sectional images and the positions (three-dimensional coordinate values) of the cross-sectional images are stored in the storage 450.

Further, for example, when the insertion route L is set on a single axial image, the image region in the axial image identified by the identifying part 430 indicates the insertion route L itself. In other words, this axial image is displayed as an image including the insertion route L. Therefore, the cross-sectional image creating part 4120c need not create cross-sectional images for this axial image.

The display controller 440 carries out various controls regarding image display. For example, the display controller 440 controls the display 460 to display the MPR images, etc. created by the rendering processing part 410c (refer to FIG. 21, FIG. 22).

Figure 22:
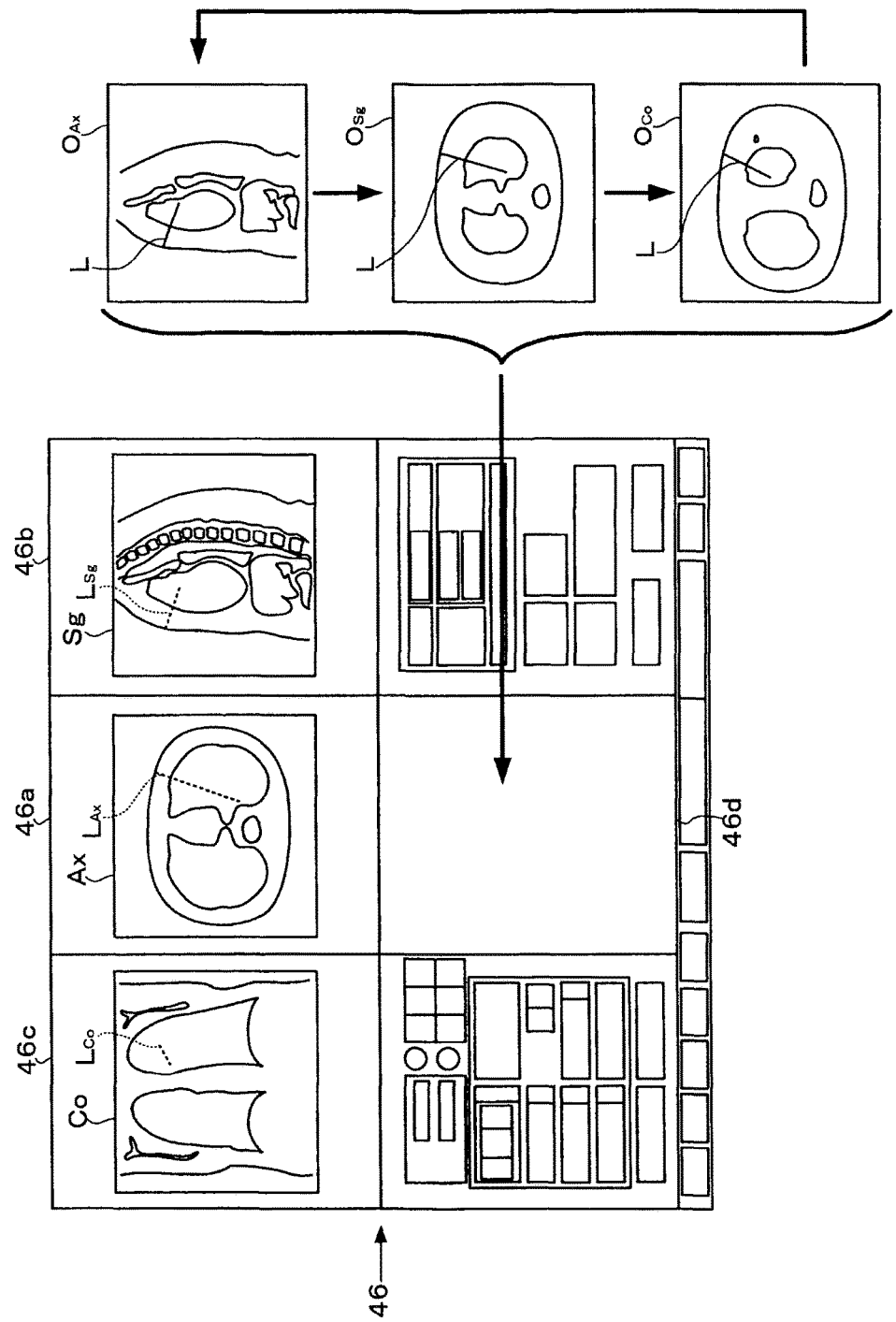
FIG. 22 is a diagram supplementing the explanation of the display controller according to the fifth embodiment.

In addition, in the present embodiment, in response to the operator's request (based on input from the input device, etc.), the display controller 440 switches and displays a plurality of cross-sectional images created by the cross-sectional image creating part 4120c on the display 460. FIG. 22 is a schematic diagram illustrating an example in which the cross-sectional images are switched and displayed on the display 460 (display screen 460d).

As described above, it is assumed that the cross-sectional image creating part 4120c creates a cross-sectional image $O_{A\_x}$, a cross-sectional image $O_{S\_g}$, and a cross-sectional image $O_{C\_o}$. In this case, the display controller 440 switches and displays in series the cross-sectional image $O_{A\_x}$, the cross-sectional image $O_{S\_g}$, and the cross-sectional image $O_{C\_o}$ on the display screen 460d of the display 460 (refer to FIG. 22). For example, the display screen 460d (or an icon displayed on the display 460, etc.) is clicked using a mouse as an example of the input device. The display controller 440 switches and displays in series the cross-sectional images based on the input signal.

These cross-sectional images are images of cross-sections including the set insertion route L. Accordingly, the operator can confirm the insertion route L in various cross-sections (various directions) by referring to these cross-sectional images. In other words, the X-ray CT system 1 in the present embodiment can display the set insertion route L so that the operator can easily understand.

Here, an example of switching the cross-sectional images in the order of the cross-sectional image $O_{A\_x}$, the cross-sectional image $O_{S\_g}$, and the cross-sectional image $O_{C\_o}$ is explained; however, the order of switching the cross-sectional images can be optionally set. Alternatively, switching may not be conducted in series. For example, when switching is set in the order of the cross-sectional image $O_{A\_x}$, the cross-sectional image $O_{S\_g}$, and the cross-sectional image $O_{C\_o}$, after the cross-sectional image $O_{S\_g}$ is displayed, the cross-sectional image $O_{A\_x}$ is sometimes confirmed again. In this case, for example, the "Back space" key of a keyboard as an example of the input device is pressed. The display controller 440 displays the cross-sectional image $O_{A\_x}$ again based on the input signal from the key board.

In addition, in the present embodiment, switching of the cross-sectional images is described; however, display of the cross-sectional images and the MPR images can be optionally set. For example, based on the input signal from the input device, the display controller 440 can switch the MPR images and the cross-sectional images and display only one of the image types (MPR images or cross-sectional images) on the display 460.

The storage 450 comprises a semiconductor storing device such as RAM, ROM, etc. The storage 450 stores the detected data, the projection data, and the CT mage data, etc. that has been provided by reconstruction processing, other than the position at which the insertion route is set.

The display 460 comprises an arbitrary display device such as an LCD, a CRT display, etc. For example, the MPR images obtained by rendering the volume data are displayed on the display 460.

The scan controller 470 controls various operations regarding X-ray scanning. For example, the scan controller 470 controls the high voltage generator 140 to apply a high voltage to the X-ray generator 110. The scan controller 470 controls the gantry driver 150 to rotatively drive the rotational body 130. The scan controller 470 controls the diaphragm driver 170 to operate the X-ray diaphragm part 160. The scan controller 470 controls the bed driver 320 to move the bed 310.

The controller 480 carries out overall control of the X-ray CT system 1 by controlling operations of the gantry device 100, the bed device 300, and the console device 400. For example, the controller 480 causes the gantry device 100 to carry out preliminary scanning as well as main scanning and acquires the detected data by controlling the scan controller 470. In addition, the controller 480 controls the processing part 410 to carry out various processing (preprocessing, reconstruction processing, etc.) on the detected data. Furthermore, the controller 480 controls the display controller 440 to display the images based on the CT image data, etc. stored in the storage 450 on the display 460.

<Operation>

Figure 23:
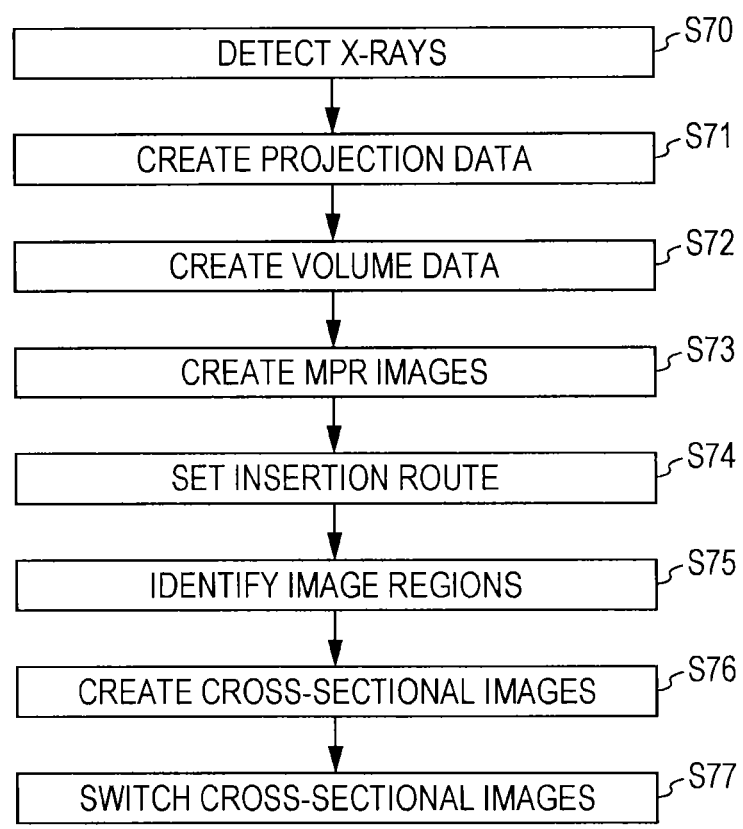
FIG. 23 is a flowchart showing the summary of operation of the X-ray CT system according to the fifth embodiment.

Next, with reference to FIG. 23, the operation of the X-ray CT system 1 according to the present embodiment will be described. Here, the operation when creating a plan for the insertion route before a biopsy is carried out using CT fluoroscopy will be described.

Before starting a biopsy, at first, the X-ray CT system 1 creates volume data V by carrying out X-ray scanning (preliminary scan) on the subject E.

Specifically, the X-ray generator 110 radiates X-rays onto the subject E. The X-ray detector 120 detects the X-rays transmitted through the subject E, and acquires the detected data (S70). The detected data detected by the X-ray detector 120 is acquired by the data acquisition part 180 and transmitted to the processing part 410 (preprocessing part 410a).

The preprocessing part 410a carries out preprocessing such as logarithmic conversion processing, offset correction, sensitivity correction, and beam hardening correction on the detected data acquired in S70 and creates projection data (S71). The created projection data is transmitted to the reconstruction processing part 410b based on the control of the controller 480.

The reconstruction processing part 410b creates a plurality of cross-sectional image data based on the projection data created in S71. In addition, the reconstruction processing part 410b creates volume data V by interpolating the plurality of cross-sectional image data (S72).

The MPR image creating part 4110c creates MPR images (axial images, sagittal images, coronal images) by rendering the volume data V created in S72 (S73).

The setting part 420 sets the insertion route L (S74) based on the axial images created in S73

Based on the insertion route L set in S74, the identifying part 430 identifies image regions (image regions $L_{A\_x}$, $L_{S\_g}$, $L_{C\_o}$) corresponding to the insertion route L in each of arbitrary axial images Ax, sagittal images Sg, and coronal images Co (S75). The display controller 440 superimposes the image region $L_{A\_x}$ identified in S75 onto the axial image Ax. The display controller 440 superimposes the image region $L_{S\_g}$ identified in S75 onto the sagittal image Sg. The display controller 440 superimposes the image region $L_{C\_o}$ identified in S75 onto the coronal images Co. The display controller 440 displays, on the display 460, the axial image Ax, the sagittal image Sg, and the coronal image Co with the image regions superimposed (refer to FIG. 22).

The cross-sectional image creating part 4120c creates cross-sectional images (cross-sectional images $O_{A\_x}$, $O_{S\_g}$, $O_{C\_o}$) of cross-sections orthogonal to the cross-sections of the MPR images with the image regions identified in S75 and along the identified image regions (S76).

The display controller 440 displays any one of the cross-sectional images created in S76 on the display screen 460d of the display 460. Upon receiving the instructions from the input device, etc., the display controller 440 switches and displays the cross-sectional images (S77; refer to FIG. 22).

Further, the processing part 410, the setting part 420, the identifying part 430, the display controller 440, the scan controller 470, and the controller 480 may be configured by, for example, a processing device (not illustrated) such as a CPU, a GPU, and an ASIC, and a storing device (not illustrated) such as ROM, RAM, and HDD. Processing programs for carrying out the functions of the processing part 410 are stored in the storing device. In addition, the setting processing programs for carrying out the functions of the setting part 420 are stored in the storing device. Moreover, the identifying processing programs for carrying out the functions of the identifying part 430 are stored in the storing device. Moreover, the display control programs carrying out the functions of the display controller 440 are stored in the storing device. Moreover, the scan control programs for carrying out the functions of the scan controller 470 are stored in the storing device. Moreover, the control programs for carrying out the functions of the controller 480 are stored in the storing device. A processing device such as a CPU carries out the function of respective parts by carrying out respective programs stored in the storing device.

<Operation and Effect>

The operation and the effect of the present embodiment will be described.

The X-ray CT system 1 of the present embodiment creates volume data based on the results obtained from scanning the subject E using X-rays. The X-ray CT system 1 has an MPR image creating part 4110c, a setting part 420, an identifying part 430, a cross-sectional image creating part 4120c, and a display controller 440. The MPR image creating part 4110c creates a first MPR image (axial image Ax) indicating a cross-section of a predetermined direction in the volume data and a second MPR image (sagittal image Sg, coronal image Co) indicating a cross-section in a different direction from the predetermined direction. The setting part 420 is used for setting an insertion route of a puncture needle for the subject E based on the first MPR image. The identifying part 430 identifies an image region (image region $L_{A\_x}$, image region $L_{S\_g}$, image region $L_{C\_o}$) corresponding to the insertion routes respectively in the first MPR image and the second MPR image. The cross-sectional image creating part 4120c creates, for each of the first MPR image and the second MPR image with the image regions identified, a cross-sectional image (cross-sectional image $O_{A\_x}$, cross-sectional image $O_{S\_g}$, cross-sectional image $O_{C\_o}$) of a cross-section orthogonal to the cross-section of the MPR image and along the image region. The display controller 440 displays the cross-sectional images on the display 460, while switching these images.

Thus, the identifying part 430 identifies the image region based on the set insertion route. The cross-sectional image creating part 4120c creates, for each of the first MPR image and the second MPR image with the image regions identified, a cross-sectional image of a cross-section orthogonal to the cross-section of the MPR image and along the image region. The display controller 440 displays the cross-sectional images on the display 460, while switching these images. The cross-sectional images are images of cross-sections including the set insertion route. Accordingly, the operator can confirm the insertion route from various directions (cross-sections) by referring to the cross-sectional images. In other words, according to the X-ray CT system 1 in the present embodiment, it becomes possible to display the images on which the insertion route of the puncture needle can be easily confirmed.

Sixth Embodiment

The configuration of the X-ray CT system 1 according to a sixth embodiment will be described with reference to FIGS. 24 to 28. In the present embodiment, the configuration in which the graphic is displayed on the display 460 is described, wherein, in response to switching of the cross-sectional images, the displayed cross-sectional position of the cross-sectional image is switched in the graphic. With respect to configuration identical to the fifth embodiment, a detailed explanation thereof is omitted.

Figure 24:
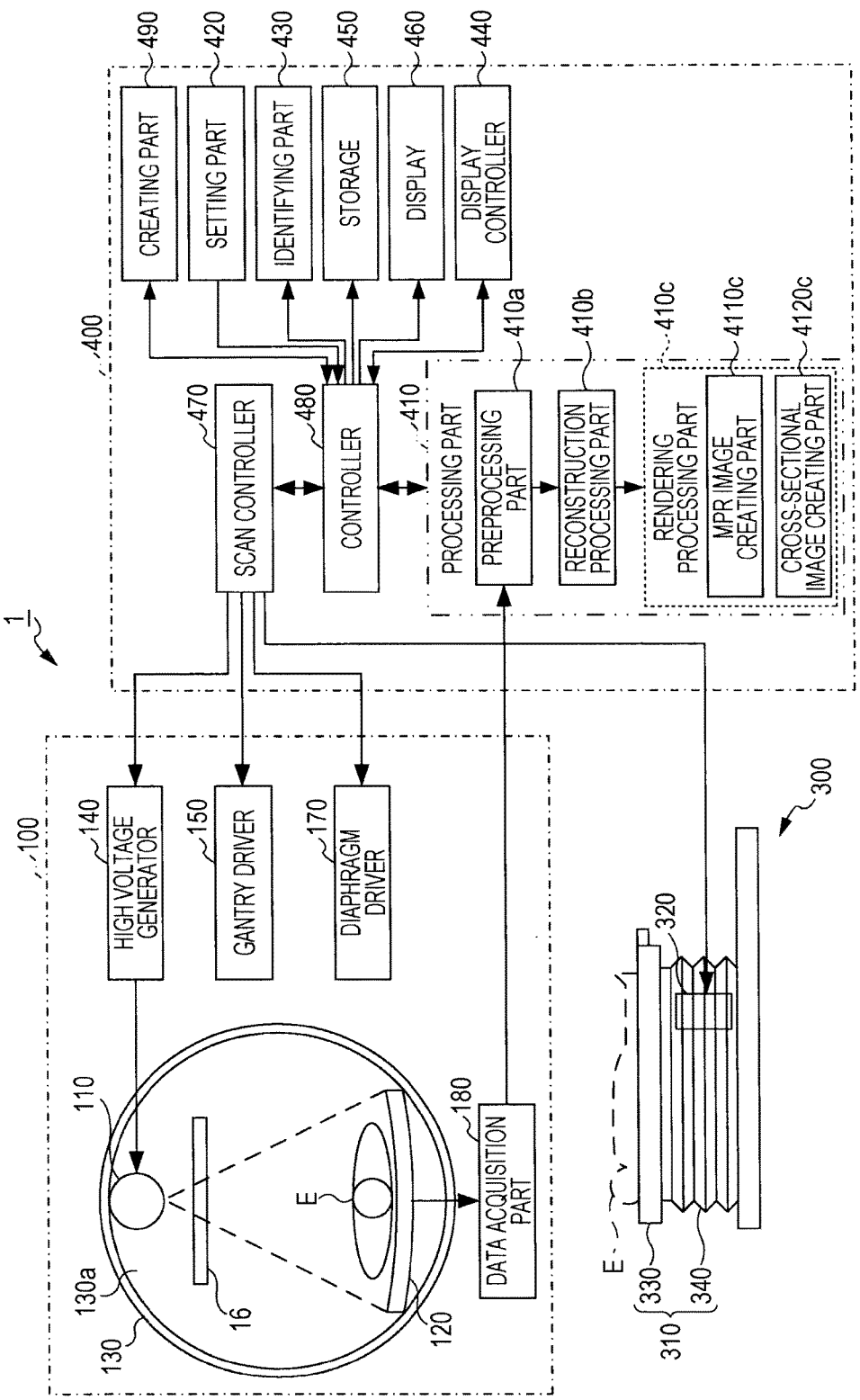
FIG. 24 is a block diagram of the X-ray CT system according to the sixth embodiment.

As illustrated in FIG. 24, the X-ray CT system 1 according to the present embodiment has a creating part 490.

The creating part 490 creates a graphic schematically indicating volume data (hereinafter, referred to as a "viewing box"). Further, as a viewing box created by the creating part 490 and a pseudo three-dimensional image of a viewing box displayed by the display controller 440 on the display 460 correspond to each other in one-to-one fashion, sometimes these are identified in the present embodiment.

As a specific example of the creating part 490, the case of creating a viewing box B based on volume data V will be described. Here, the volume data V is represented as a cube, namely, a rectangular parallelepiped with respective sides of identical lengths. In addition, it is assumed that the viewing box B and the volume data V are defined by the same coordinate system. At first, the creating part 490 extracts an outline part R of the volume data V by using a method such as edge detection (refer to FIG. 25A). Next, the creating part 490 creates a viewing box B by converting the extracted outline part R into a predetermined scale size (refer to FIG. 25B). The scale size is, for example, a value that is set in advance based on the display region, etc. of the viewing box B on the display 460.

Figure 25A:
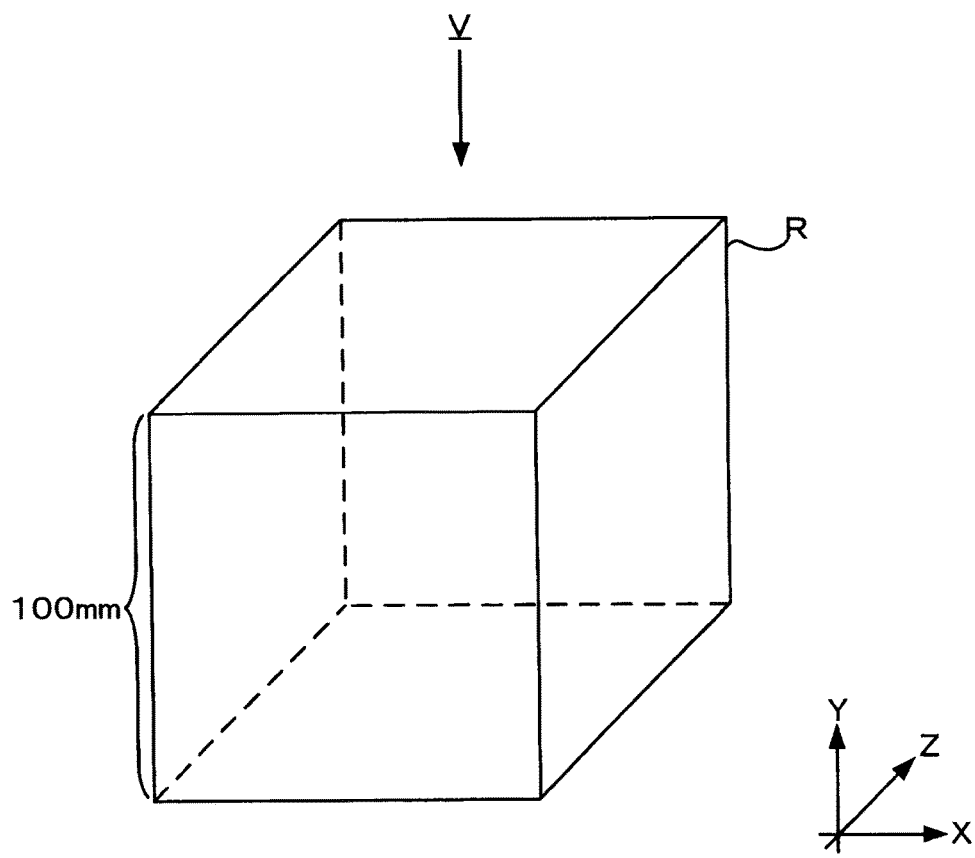
FIG. 25A is a diagram supplementing the explanation of the creating part according to the sixth embodiment.
Figure 25B:
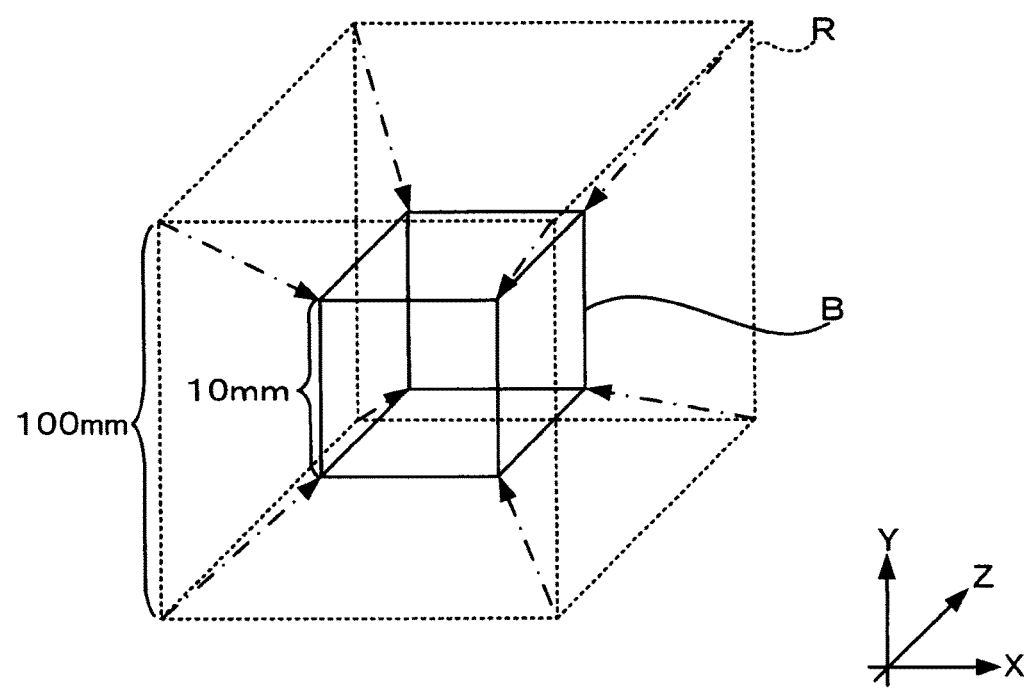
FIG. 25B is a diagram supplementing the explanation of the creating part according to the sixth embodiment.
Figure 26:
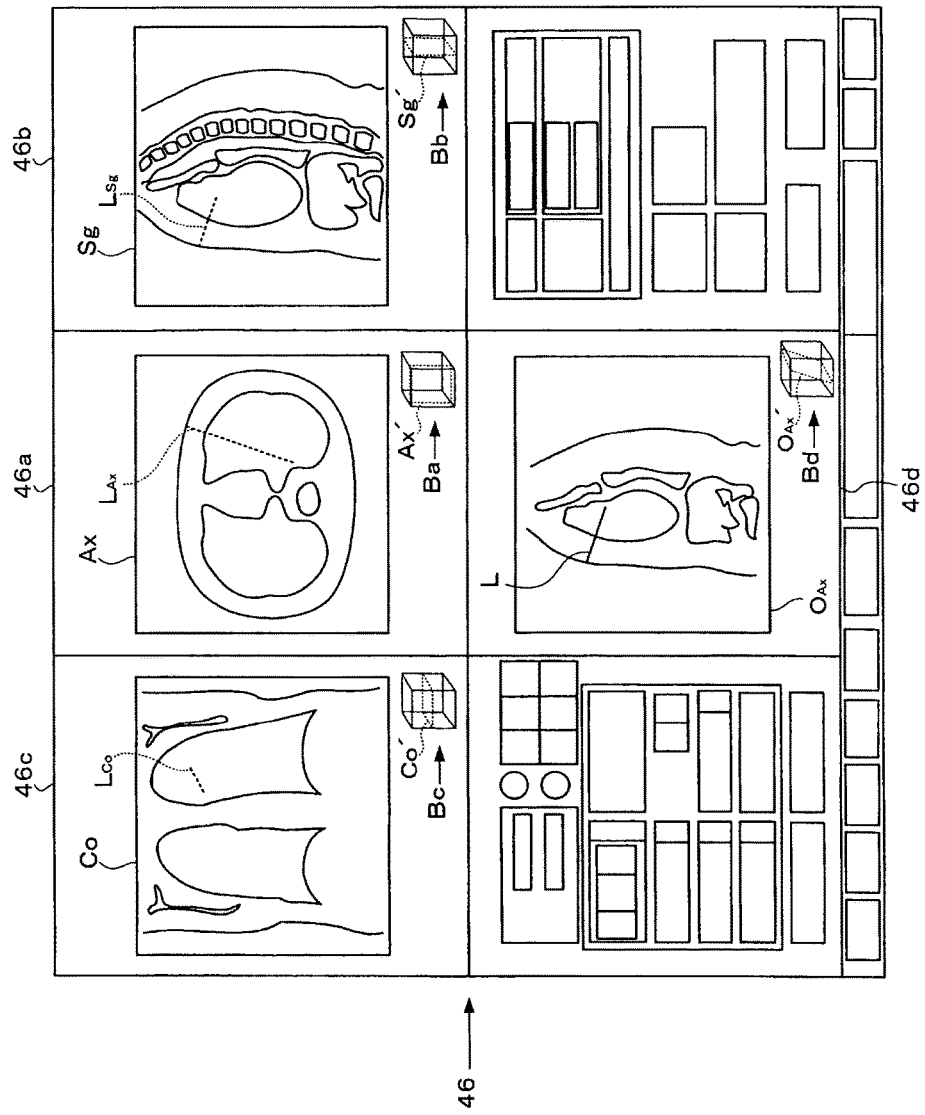
FIG. 26 is a diagram supplementing the explanation of the display controller according to the sixth embodiment.

In the present embodiment, the creating part 490 creates the viewing box B such that the respective sides of the volume data V have identical scale sizes. For example, the case in which the scale size is set to ¹⁄₁₀ is described. As illustrated in FIG. 25A, if the length of the sides of the volume data V (the outline part R) is 100 mm, the creating part 490 creates the viewing box B formed in a cubic shape with the length of the sides thereof being 10 mm based on the scale size ¹⁄₁₀ (refer to FIG. 25B).

The display controller 440 displays the graphic (the viewing box B) on the display 460. Specifically, the display controller 440 displays the viewing box B created by the creating part 490 on the display 460 as pseudo three-dimensional image. In the present embodiment, the display controller 440 displays viewing boxes Ba to Bd on display screens 460a to 460d, respectively (refer to FIG. 26). Further, the viewing boxes Ba to Bd are created based on the same volume data (volume data V).

The display controller 440 displays the cross-sectional position of the image displayed on the display 460 (to which cross-section of the volume data the displayed image correspond) in the viewing box.

For example, the display controller 440 converts the position (coordinate values) of the cross-sectional image $O_{A\_x}$ stored in the storage 450 into the same scale size as that when creating the viewing box Bd. Then, the display controller 440 identifies the position in the viewing box Bd corresponding to the converted values as a cross-sectional position $O_{A\_x}'$. The display controller 440 displays the cross-sectional position $O_{A\_x}'$ in the viewing box Bd (refer to FIG. 26). According to the same method, the display controller 440 displays the cross-sectional position Ax' corresponding to the axial image Ax in the viewing box Ba. In addition, the display controller 440 displays the cross-sectional position Sg' corresponding to the sagittal image Sg in the viewing box Bb. In addition, the display controller 440 displays the cross-sectional position Co' corresponding to the coronal image Co in the viewing box Bc.

In the present embodiment, according to the same method, the display controller 440 converts each of the positions (coordinate values) of the cross-sectional image $O_{S\_g}$ and the cross-sectional image $O_{C\_o}$ stored in the storage 450 into the same scale size as that when creating the viewing boxes. Then, the display controller 440 identifies the positions in the viewing boxes corresponding to the converted values as the cross-sectional position $O_{S\_g}'$ and the cross-sectional position $O_{C\_o}'$, respectively. The identified cross-sectional positions are stored in the storage 450.

The viewing boxes Ba to Bd and the volume data V are defined by the same coordinate system. Accordingly, the cross-sectional positions displayed in the viewing boxes Ba to Bd and the positions of the images in the volume data V are correspondingly related. In other words, the operator can easily grasp the positions of the displayed image by referring to the viewing boxes displayed in the display 460.

Figure 27:
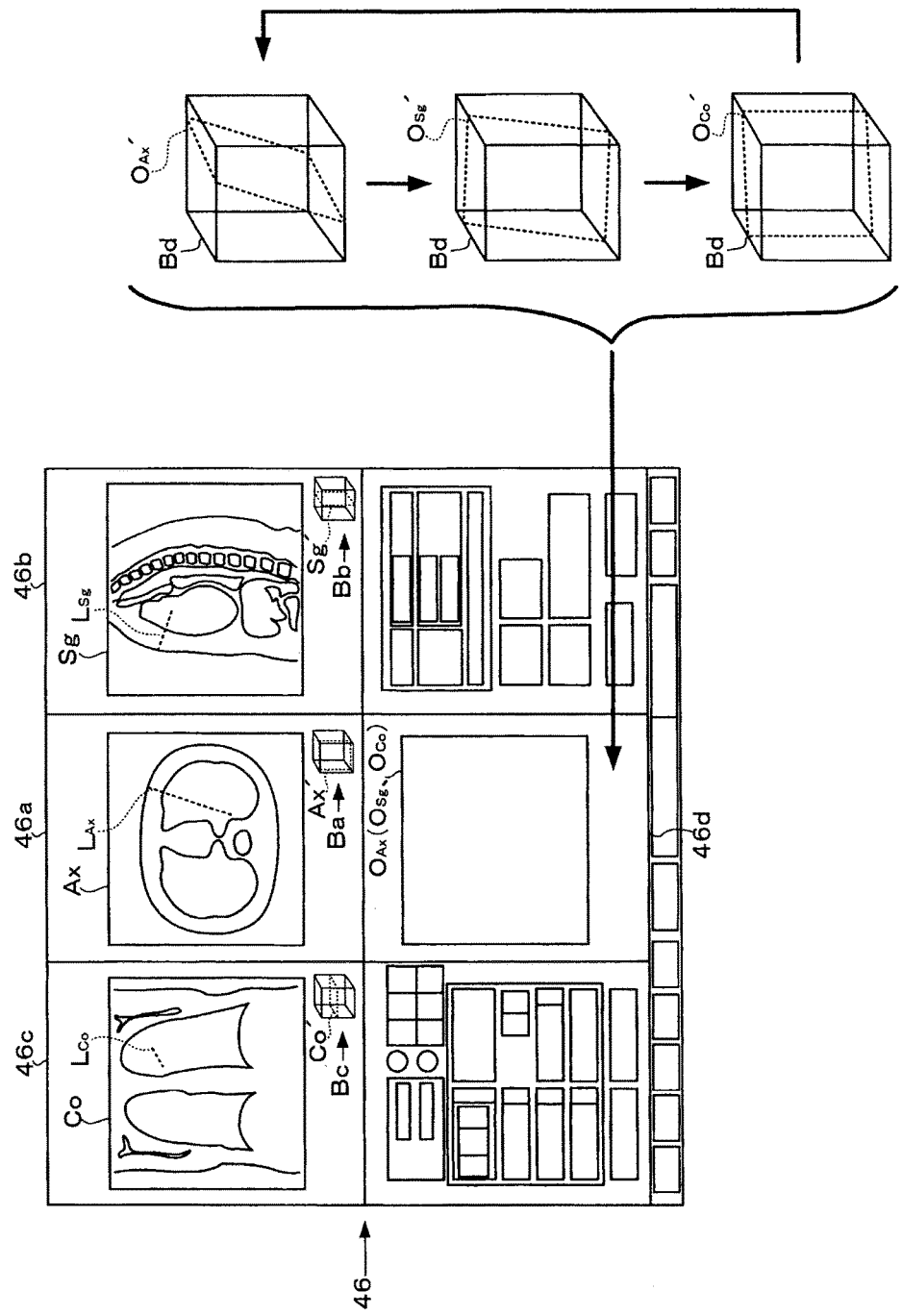
FIG. 27 is a diagram supplementing the explanation of the display controller according to the sixth embodiment.

Further, in the present embodiment, in response to the switching of cross-sectional images displayed on the display 460, the display controller 440 switches the displayed cross-sectional position of the cross-sectional image in the viewing box Bd. FIG. 27 is a schematic diagram illustrating an example in which the displayed cross-sectional positions of the cross-sectional images are switched in the viewing box Bd displayed on the display 460 (display screen 460d). Here, it is assumed that the cross-sectional image $O_{A\ x}$ is displayed on the display screen 460d. In addition, it is assumed that the order of switching the cross-sectional image is "cross-sectional image $O_{A\ x}$→cross-sectional image $O_{S\ g}$→cross-sectional image $O_{C\ o}$→cross-sectional image $O_{A\ x}$ . . . "

For example, the viewing box Bd is clicked using a mouse as an example of an input device. The display controller 440 reads the cross-sectional image $O_{S\ g}$ from the storage 450 based on an input signal thereof and displays it on the display 460 in place of the cross-sectional image $O_{A\ x}$. In this case, the display controller 440 reads the cross-sectional position $O_{S\ g}'$ corresponding to the cross-sectional image $O_{S\ g}$ to be displayed from the storage 450, and displays it on the viewing box Bd.

Further, the display controller 440 can display the cross-sectional position corresponding to the cross-sectional image and the cross-sectional position of the MPR image that is the origin of this cross-sectional image on the viewing box.

<Operation>

Figure 28:
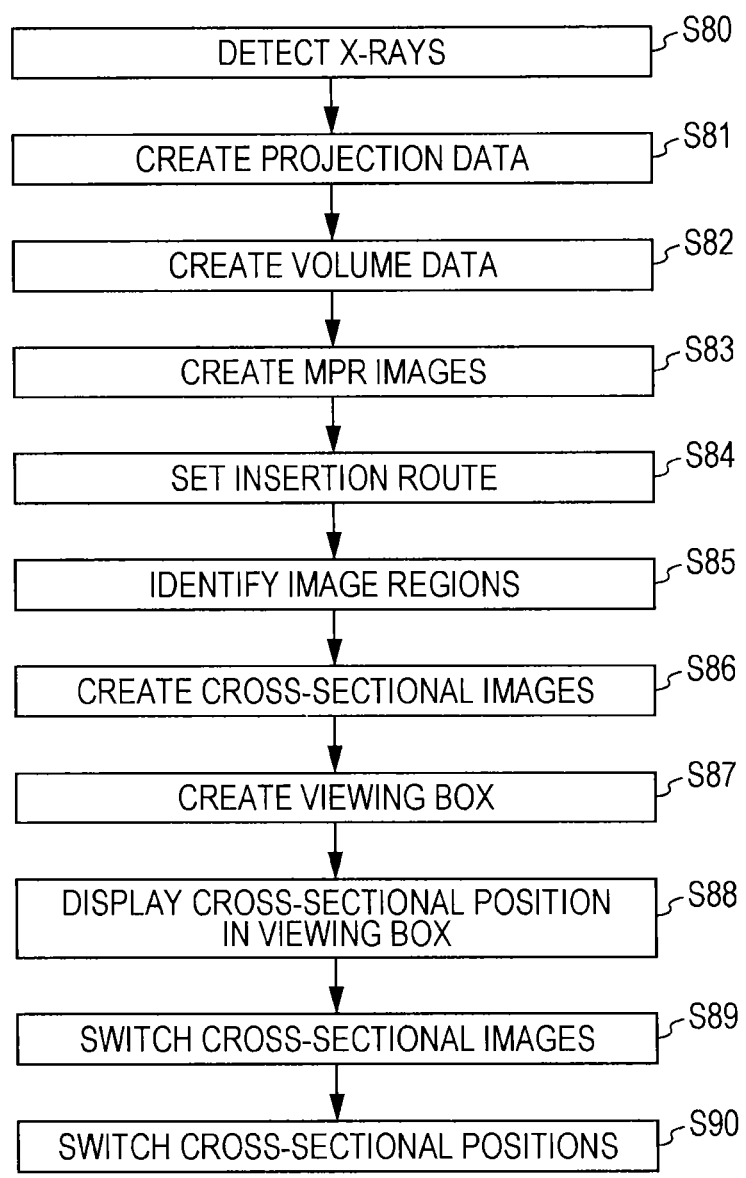
FIG. 28 is a flowchart showing the summary of the operation of the X-ray CT system according to the sixth embodiment.

Next, the operation of the X-ray CT system 1 according to the present embodiment will be described with reference to FIG. 28. Here, the operation will be described in which a plan for the insertion route is created before carrying out a biopsy using CT fluoroscopy.

Before starting a biopsy, at first, the X-ray CT system 1 carries out X-ray scanning (preliminary scanning) with respect to the subject E to create volume data V.

Specifically, the X-ray generator 110 radiates X-rays onto the subject E. The X-ray detector 120 detects the X-rays transmitted through the subject E, and acquires the detected data (S80).

The preprocessing part 410a carries out preprocessing such as logarithmic conversion processing, offset correction, sensitivity correction, and beam hardening correction on the detected data acquired in S80 and creates projection data (S81).

The reconstruction processing part 410b creates a plurality of cross-sectional image data based on the projection data created in S81. In addition, the reconstruction processing part 410b creates volume data V by interpolating the plurality of cross-sectional image data (S82).

The MPR image creating part 4110c creates MPR images (axial image, sagittal image, coronal image) by rendering the volume data V created in S82 (S83).

The setting part 420 sets the insertion route L (S84) based on the axial image created in S83.

Based on the insertion route L set in S84, the identifying part 430 identifies image regions (image regions $L_{A\ x}$, $L_{S\ g}$, $L_{C\ o}$) corresponding to the insertion route L for arbitrary axial image Ax, sagittal image Sg, and coronal image Co, respectively (S85).

The cross-sectional image creating part 4120c creates cross-sectional images (cross-sectional images $CI_{A\ x}$, $O_{S\ g}$, $O_{C\ o}$) of cross-sections orthogonal to the cross-sections of the MPR images with the image regions identified in S85 and along the identified image regions (S86).

The creating part 490 creates viewing boxes (viewing boxes Ba to Bd) based on the volume data V created in S82 (S87).

The display controller 440 displays the cross-sectional image (for example, cross-sectional image $O_{A\ x}$) created in S86 on the display screen 460d of the display 460. In addition, the display controller 440 displays the cross-sectional position corresponding to the displayed cross-sectional image on the viewing box Bd (S88). For example, the display controller 440 displays the cross-sectional position $O_{A\ x}'$ corresponding to the cross-sectional image $O_{A\ x}$ on the viewing box Bd.

Upon receiving the input of instructions through the input device, etc., the display controller 440 switches the displayed cross-sectional image (S89). For example, the display controller 440 switches the displayed cross-sectional image from the cross-sectional image $O_{A\ x}$ to the cross-sectional image $O_{S\ g}$.

In response to the switching of cross-sectional images, the display controller 440 switches the cross-sectional position displayed in the viewing box Bd to the corresponding cross-sectional position (S90). For example, the display controller 440 switches the displayed cross-sectional position from the cross-sectional position $O_{A\ x}'$ to the cross-sectional position $O_{S\ g}'$.

<Operation and Effect>

The operation and effect of the present embodiment will be described.

The display controller 440 in the X-ray CT system 1 of the present embodiment displays a graphic (viewing box) of a rectangular parallelepiped schematically indicating volume data on the display 460, and in response to the switching of the cross-sectional images, switches the cross-sectional positions of the cross-sectional images displayed in the graphic.

Thus, by displaying the cross-sectional positions of the cross-sectional images in the viewing box, and switching the cross-sectional positions in response to the switching of the cross-sectional images, it is possible to easily grasp in which direction in the volume data the currently displayed cross-sectional image faces. In other words, according to the X-ray CT system 1 of the present embodiment, it is possible to display images allowing easy grasping of the insertion route of the puncture needle, in addition to allowing the cross-sectional positions of these images to be easily grasped.

Modified Example 5

The display controller 440 can display cross-sectional images and MPR images that are the origin of the cross-sectional images in relation to each other. In this case, it is possible to easily grasp the relation between cross-sectional images and MPR images that are the origin of the cross-sectional images.

Figure 29:
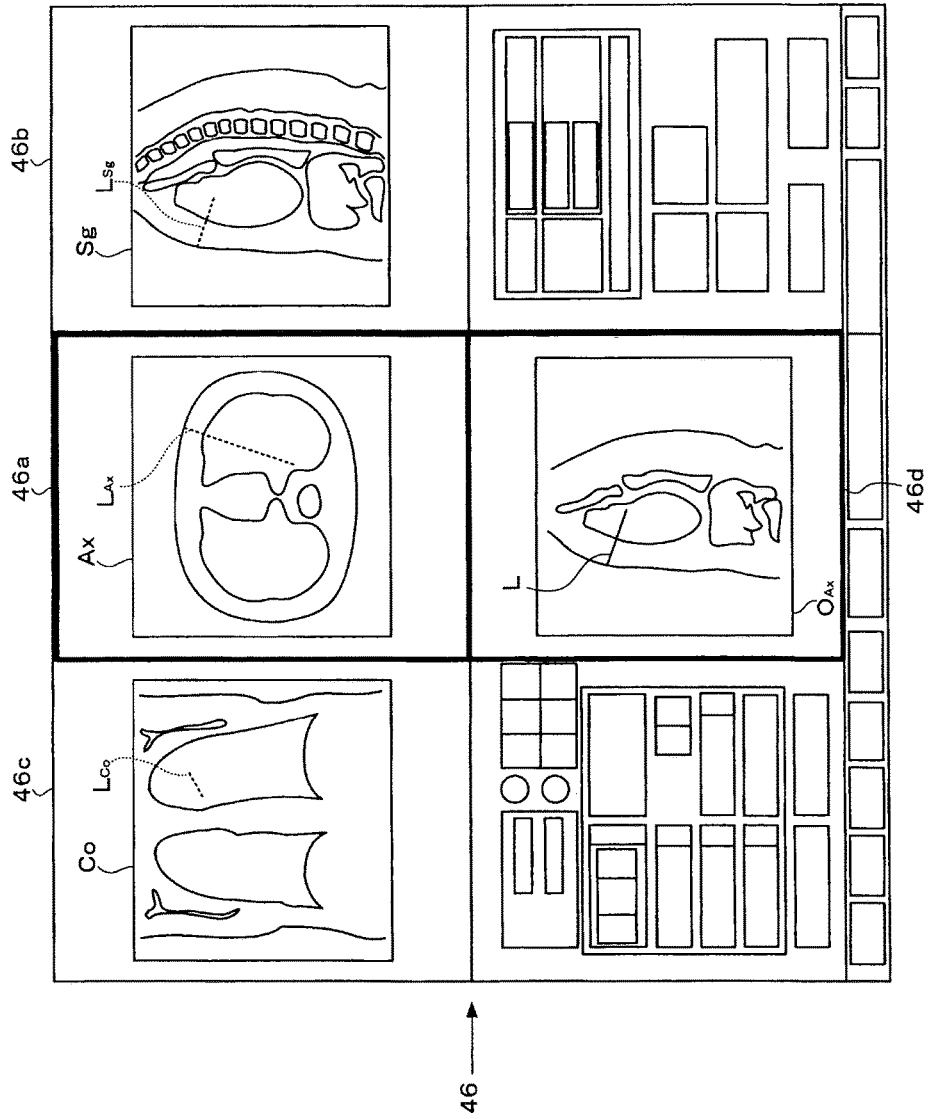
FIG. 29 is a diagram supplementing the explanation of the display controller according to Modified Example 5.

For example, when the cross-sectional image $O_{A\ x}$ is displayed on the display screen 460d, the display controller 440 can display a frame (or display region) of the display screen 460a and a frame (or display region) of the display screen 460d in the same color (refer to FIG. 29; in FIG. 29, the frame of the display screen 460a and the frame of the display screen 460d to be displayed in the same color are illustrated in bold lines).

Alternatively, the display controller 440 can display a viewing box on the display 460, and display the cross-sectional position of the cross-sectional image in the viewing box and at least part of the display region on which the MPR image that is the origin of this cross-sectional image is displayed in the same color. For example, it is possible to display the cross-sectional position $O_{A\ x}'$ in the viewing box Bd and the frame of the display screen 460a on which the axial image Ax is displayed in the same color.

In contrast, the display controller 440 can display the viewing box on the display 460, and display at least part of the display region on which the cross-sectional image is displayed and the cross-sectional position of the MPR image that is the origin of the cross-sectional image displayed in the viewing box in the same color. For example, it is possible to display the frame of the display screen 460*d* on which the cross-sectional image $O_{A\ x}$ based on the axial image Ax is displayed and the cross-sectional position Ax' of the axial image Ax in the viewing box Ba in the same color.

Modified Example 6

In addition, the storage 450 stores the cross-sectional position (coordinate values) of the created cross-sectional image in advance. Then, with respect to volume data obtained at different timings, the cross-sectional image creating part 4120*c* can create cross-sectional images based on the stored cross-sectional position. In other words, the cross-sectional image creating part 4120*c* can always create cross-sectional images at the same cross-sectional position for each of the volume data acquired at different timings. Further, in this case, it is assumed that the respective volume data is created from the same number of cross-sectional image data, and the numbers of pixels of these cross-sectional images are the same. In addition, it is assumed that the imaging conditions (imaging position, rotation speed of the rotational body 130, etc.) are equal. In other words, it is assumed that the volume data are defined by the same coordinate system.

Here, for example, in the event that the puncture needle does not travel along the insertion route L that is set based on the volume data (MPR images based on volume data), the puncture needle is not displayed on the cross-sectional image based on the volume data acquired at a different timing. For this reason, according to the configuration of the present modified example, the operator can easily grasp the deviation of the puncture needle (the deviation from the planned route).

Effects Common to the Fifth and Sixth Embodiments

According to the X-ray CT system of at least one of the above-described embodiments, the displayed cross-sectional images can be switched. Accordingly, the operator can confirm the insertion routes from various directions (cross-sections) by referring to the cross-sectional images. In other words, according to the X-ray CT system 1 in these embodiments, it is possible to display images that make it possible to easily grasp the insertion route of the puncture needle.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical apparatus, comprising:
   circuitry configured to:
      set an insertion route of a puncture needle for a subject to an image based on volume data,
      detect an outline of the volume data and scale the outline of the volume data such that the scaled outline of the volume data is a predetermined size and shape,
      according to the scaled outline of the volume data, generate a three dimensional graphic, which schematically represents the volume data, and
      display, on a display, (i) the image, (ii) the three dimensional graphic, and (iii) a route image corresponding to a direction created by converting coordinate values of the insertion route into a predetermined scale size on the three dimensional graphic.

2. The medical apparatus according to claim 1, wherein the circuitry is configured to display a cross-sectional position corresponding to a multiplanar reconstruction (MPR) image based on other volume data different from the volume data on the three dimensional graphic.

3. The medical apparatus according to claim 2, wherein the circuitry is configured to detect the puncture needle inserted into the subject based on the other volume data, and display another image corresponding to the puncture needle on the three dimensional graphic.

4. The medical apparatus according to claim 2, wherein the circuitry is configured to display the MPR image based on the other volume data on the display.

5. The medical apparatus according to claim 1, wherein the circuitry is configured to create the three dimensional graphic based on a shape of the volume data such that respective sides have identical scale sizes.

6. The medical apparatus according to claim 1, wherein the circuitry is configured to create the three dimensional graphic based on a shape of the volume data such that respective sides have different scale sizes.

7. The medical apparatus according to claim 1, wherein the circuitry is configured to:
   identify an object site to be punctured by the puncture needle based on the volume data; and
   display another image corresponding to the identified object site on the three dimensional graphic.

8. The medical apparatus according to claim 1, wherein the three dimensional graphic is a rectangular parallelepiped.

9. The medical apparatus according to claim 1, wherein the circuitry is configured to create a fan-shaped graphic schematically indicating the volume data and display the fan-shaped graphic.

10. A medical apparatus, comprising:
    circuitry configured to:
       set an insertion route of a puncture needle for a subject to a multiplanar reconstruction (MPR) image based on volume data,
       detect an outline of the volume data and scale the outline of the volume data such that the scaled outline of the volume data is a predetermined size and shape,
       according to the scaled outline of the volume data, generate a three dimensional graphic, which schematically represents the volume data, and
       display, on a display, (i) the MPR image, (ii) the three dimensional graphic, and (iii) a route image corresponding to a direction created by converting coordinate values of the insertion route into a predetermined scale size on the three dimensional graphic and a cross-sectional position corresponding to the MPR image on which the insertion route is set on the three dimensional graphic.

11. An X-ray computed tomography (CT) system for creating volume data based on results obtained from scanning a subject, comprising:
    circuitry configured to:

create a first multiplanar reconstruction (MPR) image indicating a cross-section in a predetermined direction to the volume data and a second MPR image indicating cross-sections in a different direction from the predetermined direction, set an insertion route of a puncture needle for the subject based on the first MPR image, detect an outline of the volume data and scale the outline of the volume data such that the scaled outline of the volume data is a predetermined size and shape, according to the scaled outline of the volume data, generate a three dimensional graphic, which schematically represents the volume data, identify an image region where the insertion route is projected on each of the cross-section of the first MPR image and the cross-sections of the second MPR image, create, for each of the first MPR image and the second MPR image with image regions identified, a cross-sectional image of a cross-section orthogonal to the cross-section of a corresponding MPR image and along a corresponding image region, and display, on a display, (i) the cross-sectional images, (ii) the three dimensional graphic, and (iii) a route image corresponding to a direction represented by the three dimensional graphic and created by converting coordinate values of the insertion route into a predetermined scale size on the three dimensional graphic, and the cross-sectional images on the display while switching these cross-sectional images.

12. The X-ray CT system according to claim 11, wherein the circuitry is configured to display, on the display, the first MPR image and the second MPR image with the identified image regions superimposed.

13. The X-ray CT system according to claim 11, wherein the circuitry is configured to display cross-sectional positions of the cross-sectional images while switching the cross-sectional positions in the three dimensional graphic in response to the switching of the cross-sectional images.

14. The X-ray CT system according to claim 11, wherein the circuitry is configured to display the cross-sectional images and the first MPR image and the second MPR image that are origins of the cross-sectional images in relation to each other.

15. The X-ray CT system according to claim 14, wherein the circuitry is configured to display cross-sectional positions of the cross-sectional images in the three dimensional graphic and at least part of display regions on which the first MPR image and the second MPR image that are the origins of the cross-sectional images are displayed in a same color.

16. The X-ray CT system according to claim 14, wherein the circuitry is configured to display at least part of display regions on which the cross-sectional images are displayed and cross-sectional positions of the first MPR image and the second MPR image that are the origins of the cross-sectional images in a same color.

17. The X-ray CT system according to claim 11, wherein the circuitry is configured to create any one of an axial image, a sagittal image, a coronal image, and an oblique image of the subject as the first MPR image.

18. The X-ray CT system according to claim 11, wherein the set insertion route is based on a plurality of first MPR images.

* * * * *